(12) United States Patent
Hayes et al.

(10) Patent No.: US 10,087,464 B2
(45) Date of Patent: Oct. 2, 2018

(54) COMPOSITIONS AND METHODS FOR DELIVERING NUCLEIC ACID TO A CELL

(71) Applicant: MERRIMACK PHARMACEUTICALS, INC., Cambridge, MA (US)

(72) Inventors: Mark E. Hayes, San Francisco, CA (US); Dmitri B. Kirpotin, Revere, MA (US)

(73) Assignee: Merrimack Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/004,481

(22) Filed: Jan. 22, 2016

(65) Prior Publication Data

US 2016/0138044 A1  May 19, 2016

Related U.S. Application Data

(63) Continuation of application No. 13/967,664, filed on Aug. 15, 2013, now abandoned, which is a continuation of application No. PCT/US2012/025324, filed on Feb. 15, 2012.

(60) Provisional application No. 61/443,246, filed on Feb. 15, 2011.

(51) Int. Cl.
| | |
|---|---|
| *C12N 15/88* | (2006.01) |
| *A61K 48/00* | (2006.01) |
| *C12N 15/113* | (2010.01) |
| *A61K 9/127* | (2006.01) |
| *A61K 47/69* | (2017.01) |

(52) U.S. Cl.
CPC ............ *C12N 15/88* (2013.01); *A61K 9/1271* (2013.01); *A61K 47/6913* (2017.08); *A61K 48/0033* (2013.01); *C12N 15/113* (2013.01); *C12N 2310/14* (2013.01); *C12N 2310/531* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 5,908,635 | A | 6/1999 | Thierry |
| 6,210,707 | B1 | 4/2001 | Papahadjopoulos et al. |
| 6,794,128 | B2 | 9/2004 | Marks et al. |
| 7,244,826 | B1 | 7/2007 | Marks et al. |
| 7,507,407 | B2 | 3/2009 | Benz et al. |
| 7,780,882 | B2 | 8/2010 | Chang et al. |
| 7,846,440 | B2 | 12/2010 | Schoeberl et al. |
| 2007/0171077 | A1 | 7/2007 | Kawarizadeh |
| 2007/0212403 | A1 | 9/2007 | Barenholz et al. |
| 2010/0278885 | A1 | 11/2010 | Ikeda et al. |

FOREIGN PATENT DOCUMENTS

| | | |
|---|---|---|
| JP | 10-506395 A | 6/1998 |
| JP | 10506395 A | 6/1998 |
| JP | 200545843 A | 6/2005 |
| JP | 2010207157 A | 9/2010 |
| JP | 2011-500520 A | 1/2011 |
| WO | 199610392 A1 | 4/1996 |
| WO | 2008096779 A1 | 8/2008 |
| WO | WO2009047006 A2 | 4/2009 |
| WO | WO2009061515 A1 | 5/2009 |
| WO | 2010045512 A2 | 4/2010 |
| WO | WO2010125544 A1 | 11/2010 |

OTHER PUBLICATIONS

Bloomfield (1998) "DNA Condensation by Multivalent Cations", Biopolymers, 44: 269-82.*
Heyes, M. E., et al. "Genospheres: self-assembling nucleic acid-lipid nanoparticles suitable for targeted gene delivery" Gene Therapy (2006) 13, pp. 646-651.
Feuerstein, Burt G., et al. "Spermine-DNA interactions: A theoretical study" Proc. Natl. Acad. Sci, USA, vol. 83, pp. 5948-5952, Aug. 1986 Biophysics.
Morrissey, David V., et al. "Potent and persistent in vivo anti-HBV activity of chemically modified siRNAs" Nature Biotechnology, vol. 23, No. 8 (2005), pp. 1002-1007.
Thurston, Gavin, et al. "Cationic Liposomes Target Angiogenic Endothelial Cells in Tumors and Chronic Inflammation in Mice" J. Clin. Invest., vol. 101., No. 7 (1998), pp. 1401-1413.
Lee, Robert J., et al., "Folate-targeted, Anionic Liposome-entrapped Polylysine-condensed DNA for Tumor Cell-specific Gene Transfer" The Journal of Biological Chemistry, vol. 271 (1996), pp. 8481-8487.
Drake, Christopher R., et al. "Bioresponsive Small Molecule Polyamines as Noncytotoxic Alternative to Polyethylenimine" Molecular Pharmaceutics, vol. 7, No. 6 (2010), pp. 2040-2055.
Dewa, Takehisa, et al. "Liposomal Polyamine-Dialkyl Phosphate Conjugates as Effective Gene Carriers: Chemical Structure, Morphology, and Gene Transfer Activity" Bioconjugate Chem., vol. 21 (2010), pp. 844-852.
Randazzo, R. A. S., et al. "A series of cationic sterol lipids with gene transfer and bactericidal activity" Bioorganic & Medicinal Chemistry, vol. 17 (2009), pp. 3257-3265.
Ghonaim, H. M., et al. "Very Long Chain N4, N9-Diacyl Spermines: Non-Viral Lipopolyamine Vectors for Efficient Plasmid DNA and siRNA Delivery" Pharmaceutical Research, vol. 26, No. 1, (2009), pp. 19-31.
Eliyahu, H., et al. "Dextran-spermine-based polyplexes—Evaluation of transgene expression and of local and systemic toxicity in mice" Biomaterials, vol. 27 (2006), pp. 1636-1645.
International Search Report of PCT/US2012/025324, dated Dec. 26, 2012.
International Preliminary Report on Patentability and Written Opinion of PCT/US2012/025324, dated Dec. 26, 2012.

(Continued)

*Primary Examiner* — Robert M Kelly
(74) *Attorney, Agent, or Firm* — Honigman Miller Schwartz and Cohn LLP; Cynthia M. Bott; Jonathan P. O'Brien

(57) ABSTRACT

Provided are novel compositions useful for delivering nucleic acids to cells. Also provided are methods for making and using such compositions.

6 Claims, 12 Drawing Sheets

(56) References Cited

OTHER PUBLICATIONS

Heyes, J., et al. "Lipid Encapsulation Enables the Effective Systemic Delivery of Polyplex Plasmid DNA" Molecular Therapy, vol. 15 (2007), pp. 713-720.
European Supplementary Search Report dated Apr. 5, 2015 for EP12746634.
Hou, et al. Methods to improve DNA condensation efficiency by alkali treatment. Nucleosides, Nucleotides, and Nucleic Acids (2009) 28(8): 725-735 (Abstract Only).
Won, et al. Reducible Poly(oligo-D-arginine) for Enhanced Gene Expression in Mouse Lung by Intratracheal Injection. (Dec. 2010) Molecular Therapy 18(4): 734-742.

* cited by examiner

Time course of temperature equilibration of 50 vol.% ethanol solution, after immersion in 60°C oil bath.

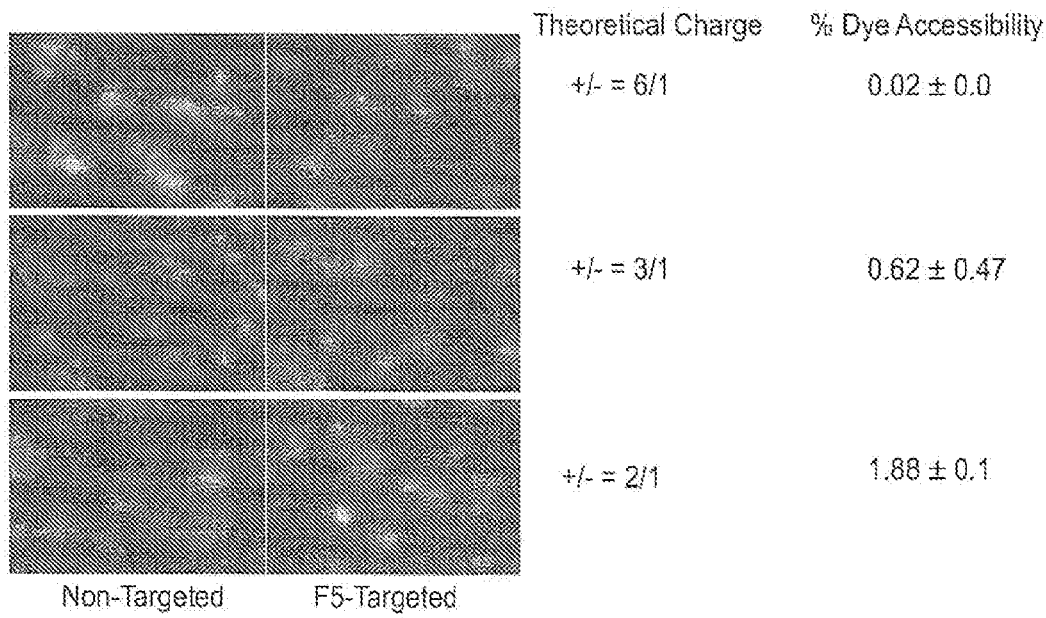
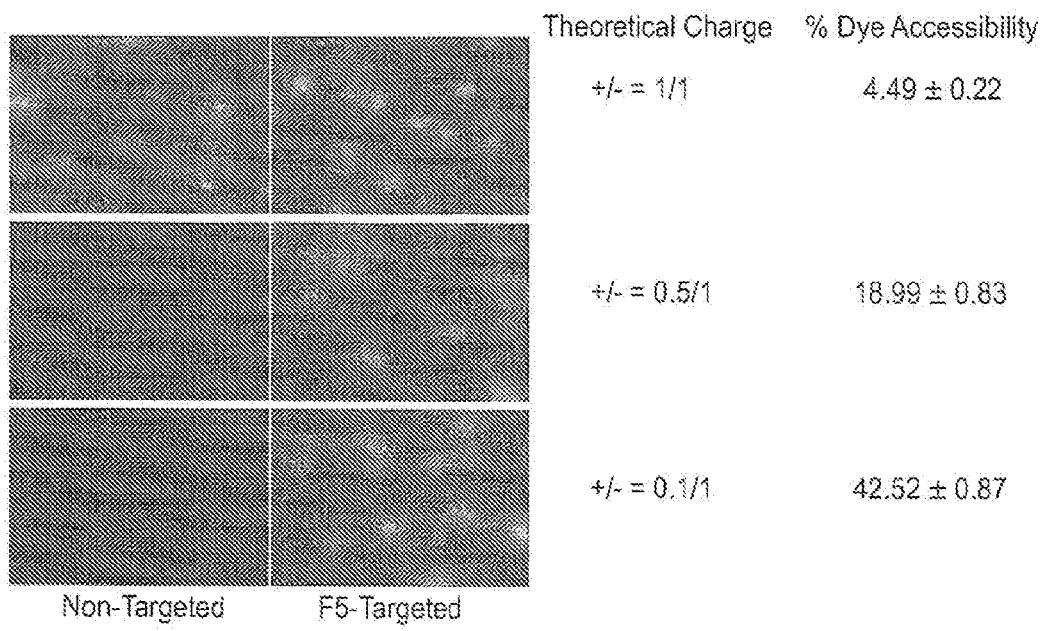
Fluorescent microscopy of cells treated with liposomes (Her2 targeted and plain non-targeted) for 24h. (1 sec exposure using Rh filter set). The values on the right indicate the theoretical charge, determined by taking the ratio of cationic lipid to DNA, and the % dye accessibility which indicates the % DNA entrapped within the particle.
FIG. 3

The chemical structures of spermine, a typical phospholipid, dioleoyl-sn-glycero-phosphatidylcholine (DOPC) and a 3D depiction of spermine interaction with DNA double helix.

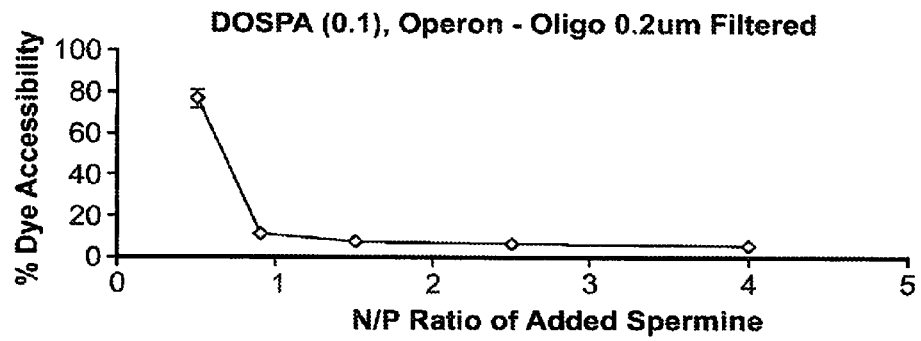

Entrapment analysis of liposomes containing a fixed amount of cationic lipid in the formulation to bind 10% of the available anionic phosphates charges in addition to varying amounts of spermine.

FIG. 6A

| Dospa (0.1) | Sample# | N/P | Size nm | stdev | % Filtered |
|---|---|---|---|---|---|
| post - dialys | 1 | 0.5 | 120.90 | 47.40 | |
| | 2 | 0.9 | 120.90 | 47.90 | |
| | 3 | 1.5 | 124.60 | 50.40 | |
| | 4 | 2.5 | 133.40 | 49.70 | |
| | 5 | 4.0 | 139.00 | 55.00 | |
| 0.2uM filt | 1 | 0.5 | 116.60 | 49.40 | 85.92 |
| | 2 | 0.9 | 112.50 | 44.90 | 99.57 |
| | 3 | 1.5 | 116.90 | 46.90 | 95.98 |
| | 4 | 2.5 | 124.00 | 47.50 | 91.58 |
| | 5 | 4.0 | 133.30 | 50.70 | 91.91 |

Table displaying liposome size before and after sterile filtering through a 0.2um PES filter and filtering efficiency.

FIG. 6B

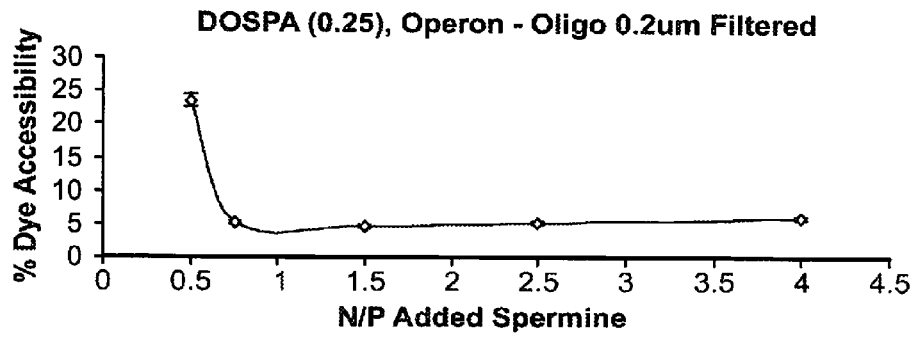

Entrapment analysis of liposomes containing a fixed amount of cationic lipid in the formulation to bind 25% of the available anionic phosphates charges in addition to varying amounts of spermine.

FIG. 7A

| Dospa (0.25) | Sample# | N/P | Size nm | stdev | %Filtered |
|---|---|---|---|---|---|
| post - dialys | 6 | 0.5 | 107.60 | 45.20 | |
| | 7 | 0.8 | 114.30 | 44.70 | |
| | 8 | 1.5 | 112.10 | 46.90 | |
| | 9 | 2.5 | 127.20 | 51.60 | |
| | 10 | 4.0 | 151.50 | 50.30 | |
| 0.2um filtered | 6 | 0.5 | 110.60 | 46.40 | 78.69 |
| | 7 | 0.8 | 112.00 | 47.70 | 79.57 |
| | 8 | 1.5 | 112.70 | 47.10 | 82.47 |
| | 9 | 2.5 | 127.30 | 49.90 | 87.02 |
| | 10 | 4.0 | 148.40 | 52.70 | 86.68 |

Table displaying liposome size before and after sterile filtering through a 0.2um PES filter and filtering efficiency.

FIG. 7B

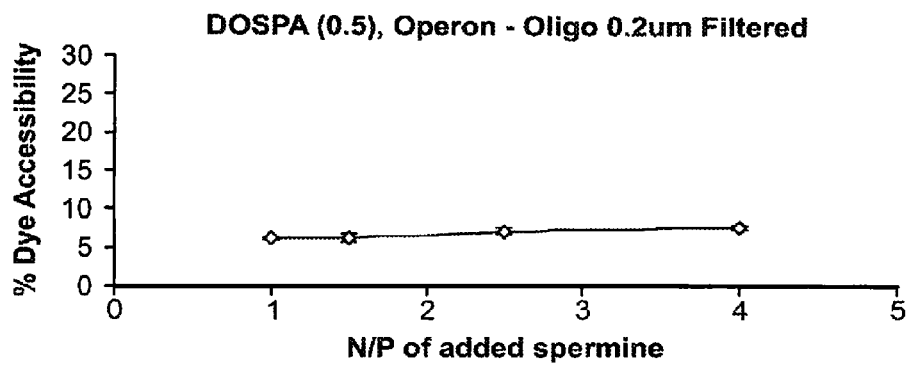

Entrapment analysis of liposomes containing a fixed amount of cationic lipid in the formulation to bind 50% of the available anionic phosphates charges in addition to varying amounts of spermine.

FIG. 8A

| Dospa (0.5) | Sample# | N/P | Size nm | stdev | % Filtered |
|---|---|---|---|---|---|
| post - dialys | 11 | 0.5 | 107.40 | 42.60 | |
| | 12 | 1.5 | 120.30 | 46.50 | |
| | 13 | 2.5 | 123.30 | 48.40 | |
| | 14 | 4.0 | 129.50 | 50.50 | |
| 0.2um | 11 | 0.5 | 105.40 | 42.30 | 84.17 |
| filtered | 12 | 1.5 | 116.60 | 47.10 | 93.78 |
| | 13 | 2.5 | 121.90 | 49.70 | 90.04 |
| | 14 | 4.0 | 125.10 | 51.80 | 95.98 |

Table displaying liposome size before and after sterile filtering through a 0.2um PES filter and filtering efficiency.

FIG. 8B

Microscopy of MCF7/clone18 cells after 24h exposure to DiI(3)-DS labeled liposomes-DOSPA (0.1) Formulation (1/4 sec fluorescence; 8 sec phase contrast). NT designates plain, "non-targeted" formulations, T "targeted" anti-Her2 receptor formulations. N/P indicates the nitrogen / phosphate ratio of DOSPA/DNA respectively.

Microscopy of MCF7/clone18 cells after 24h exposure to DiI(3)-DS labeled liposomes-DOSPA (0.25) Formulation (1/4 sec fluorescence; 8 sec phase contrast). NT designates plain, "non-targeted" formulations, T "targeted" anti-Her2 receptor formulations. N/P indicates the nitrogen / phosphate ratio of DOSPA/DNA respectively.

Microscopy of MCF7/clone18 cells after 24h exposure to DiI(3)-DS labeled liposomes-DOSPA (0.25) Formulation (1/4 sec fluorescence; 8 sec phase contrast). NT designates plain, "non-targeted" formulations, T "targeted" anti-Her2 receptor formulations. N/P indicates the nitrogen / phosphate ratio of DOSPA/DNA respectively.

SDS-PAGE gel showing purified liposome samples and standards containing varying amounts of F5-PEG-DSPE. The density of the gel bands was determined using Image J software. From extrapolation to the standard curve, the amount of incorporated protein per umol of lipid was 13.64 ± 0.64 and 10.59 ± 0.39 ug/umol for the N/P = 1.5 and N/P = 3.0 respectively (in duplicate)

Absorbance at 260nm of various siRNA solutions at temperatures.

SDS-PAGE gel showing F5-PEG-DSPE content of purified liposomes that were heated at various temperatures to test insertion efficiency of targeting conjugate.

COMPOSITIONS AND METHODS FOR DELIVERING NUCLEIC ACID TO A CELL

RELATED APPLICATIONS

This application is a continuation of U.S. patent application Ser. No. 13/967,664, filed Aug. 15, 2013, now abandoned, which is a continuation of PCT International Application No. PCT/US2012/025324, filed Feb. 15, 2012, which claims the benefit of U.S. Provisional Patent Application No. 61/443,246, filed Feb. 15, 2011. The contents of each of the foregoing applications are incorporated herein by reference in their entirety.

BACKGROUND OF THE INVENTION

Introducing nucleic acids into living cells is an important process in modern biological research, industry, and medicine. Efficient delivery of a functional nucleic acid into a living cell is an indispensable component of genetic engineering, recombinant protein production, and medical technologies known as gene therapy.

For example, gene therapy involves the transfer of normal, functional genetic material into specific cells to correct an abnormality due to a deficient or defective gene product. A variety of methods have been developed to facilitate both in vivo, in vitro, or ex vivo gene transfer.

Nucleic acid therapies involve the transfer of natural or synthetic oligonucleotides and polynucleotides into normal and/or pathological cells with the purpose of correcting or eliminating the diseased cells. For example, antisense oligonucleotides and interfering RNAs such as siRNAs and shRNAs are used to block undesirable pathways of protein expression in the cells. Plasmids, e.g., plasmids that comprise one or more protein-encoding sequences, may be introduced into cells to correct a cellular defect associated with a defective or absent gene or gene product, or to induce tumor cell death. Polynucleotide inductors of immunity, such as poly(I, C) or oligo- and polynucleotides having methylated GC pairs are used to increase the patients' defense against pathogens such as viruses or cancer cells. Ribozymes are ribonucleic acids that catalyze selective degradation of other polynucleotides in the diseased cells, for example, in cancer or virus-infected cells. Because oligo- and polynucleotides generally have low permeability through cell membranes, and are quickly eliminated from the body, there is the need for oligo/polynucleotide delivery vehicles that would allow enhanced intracellular delivery and protection from degradation and/or elimination from the body.

One useful method for providing nucleic acid therapies is to encapsulate therapeutic nucleic acids into liposomes suitable for administration to a patient. Liposome technology has been developed and commercialized for the delivery of conventional pharmaceutical agents, but to date therapeutic nucleic acid containing liposomes have not been commercialized. To date many publications demonstrate that liposome-plasmid DNA complexes can mediate efficient transient expression of a gene in cultured cells but poor in vivo transfection efficiencies. Unlike viral vector preparations, liposome-nucleic acid complexes can have insufficient stability, and thus can be unsuitable for systemic injection.

The ability of a liposome to deliver a nucleic acid to a cell can be enhanced by adding adequate levels of cationic lipids to the lipid bilayer of the liposome, but cationic lipids are not cell specific. Because many diseases, such as cancers, are limited to specific organs, tissues, or cell types, it is desirable to transfer nucleic acids in an organ, tissue, or cell selective fashion. Immunoliposomes—liposomes comprising exterior antibody functionalities, are capable of achieving such cell selective transfer of nucleic acids to cells. The presence of large amounts of cationic lipids on liposomes a useful for achieving introduction of a therapeutic entity within the liposome into a cell. In immunoliposomes however, amounts of cationic lipids that are effective to achieve such an effect can result in undesirable non-specific binding to cells, which decreases the ability to specifically direct a liposome-nucleic acid complex to a target cell or cell type.

It would be desirable to have improved small, active, and biocompatible liposome-nucleic acid complexes that are capable of being prepared as or converted to immunoliposomes selectively targeted to specific cell types and methods for making and such complexes.

SUMMARY OF THE INVENTION

The present invention relates to liposome-nucleic acid complexes and to methods of making and using such complexes.

In one aspect, a method for preparing a liposome comprising a nucleic acid and a lipid component, the method comprising: combining a lipid component and a nucleic acid component in a mixture comprising: water; a water-miscible organic solvent; and a polyamine; under conditions such that a liposome comprising the nucleic acid and the lipid component is formed.

In certain embodiments, the polyamine is an oligoethyleneimine, a polyethyleneimine, or a polyamino$C_2$-$C_{10}$alkane. In certain embodiments, the polyamine is selected from the group consisting of spermine, spermidine, and putrescine. In certain embodiments, the polyamine is spermine.

In certain embodiments, the nucleic acid is DNA. In other embodiments, the nucleic acid is RNA. In certain embodiments, the RNA is siRNA. In certain embodiments, the RNA is shRNA. In other embodiments the RNA is a double-stranded dicer substrate RNA.

In certain embodiments, the lipid component comprises a non-cationic lipid. In certain embodiments, the non-cationic lipid is a neutral lipid. In certain embodiments, the neutral lipid comprises DOPC, DOPE, cholesterol, or PEG-DSG.

In certain embodiments, the liposome further comprises a cationic lipid. In certain embodiments, the cationic lipid comprises DOTAP or DOSPA. In certain other embodiments the lipid component contains no cationic lipid.

In certain embodiments, the water-miscible organic solvent comprises methanol, ethanol, 1-propanol, or 2-propanol. In certain embodiments, the water-miscible organic solvent comprises ethanol. In certain embodiments, the ratio of water to water-miscible organic solvent is between about 2:1 and 1:2. In certain embodiments, the ratio of water to water-miscible organic solvent is about 1:1.

In certain embodiments, the ratio of polyamine nitrogen to nucleic acid phosphate groups (N/P) is at least about 0.5. In certain embodiments, N/P is between about 0.8 and about 1.5.

In certain embodiments, the step of combining is performed at a temperature not greater than about 60° C. In certain embodiments, the step of combining is performed at a temperature between about 40° C. and about 50° C.

In certain embodiments, the lipid component comprises a cationic lipid and the ratio of cationic lipid nitrogen to nucleic acid phosphate groups (N/P) is about 0.5 or less.

In certain embodiments, the lipid component comprises a neutral phospholipid and no cationic lipid, and wherein the nucleic acid and the lipid component are present at a ratio of from 5 nmol lipid per microgram of the nucleic acid to 20, 30, 40, 50, 60, 70, 80, 90, or 100 (optionally 5-20 or 30, preferably 10) nmol lipid per microgram of the nucleic acid, and wherein the liposome is from 30 to 500 nanometers in diameter.

In certain embodiments, the step of combining is performed at a pH not less than about 6.5. In certain embodiments, the step of combining is performed at a pH between about 7.0 and about 8.0. In certain embodiments where the liposomes will comprise RNA, the step of combining is performed at a pH between about 5.5 and about 6.5.

In another aspect, the invention provides a composition comprising a liposome in an aqueous medium, the liposome having an interior and an exterior, wherein the liposome comprises: a nucleic acid; a polyamine; and a lipid component;

wherein the lipid component comprises a neutral phospholipid and essentially no cationic lipid, and wherein the nucleic acid and the lipid component are present at a ratio of from 5 nmol lipid per microgram of the nucleic acid to 20, 30, 40, 50, 60, 70, 80, 90, or 100 (optionally 5-20 or 30, preferably 10) nmol lipid per microgram of the nucleic acid, and wherein the liposome is from 30 to 500 nanometers in diameter.

In certain embodiments, the polyamine is oligoethyleneimine, polyethyleneimine, or a polyamino$C_2$-$C_{10}$alkane. In certain embodiments, the polyamine is selected from the group consisting of spermine, spermidine, and putrescine. In certain embodiments, the polyamine is spermine.

In certain embodiments, the nucleic acid is DNA. In other embodiments, the nucleic acid is RNA. In certain embodiments, RNA is siRNA. In certain embodiments, the RNA is shRNA.

In certain embodiments, the non-cationic lipid comprises DOPC, DOPE, cholesterol, PEG-DSG. In certain embodiments, the lipid component is essentially free of cationic lipid (e.g., has less than 0.1% cationic lipid by weight).

In other embodiments, the lipid component comprises a cationic lipid and a non-cationic lipid. In certain embodiments, the cationic lipid comprises DOTAP or DOSPA.

In certain embodiments, the liposome is from 70 to 300 nanometers in diameter.

In another aspect, a method of using of a liposome provided herein is provided, the method comprising: attaching an internalizing antibody or a fragment thereof, which antibody or fragment binds to a specific cell surface antigen, to the exterior of the liposome, wherein the liposome with the antibody attached is internalized by a cell expressing at least 100,000 or at least 1,000,000 molecules of the antigen when contacted and incubated with the cell under internalizing conditions.

In certain embodiments, internalization of the liposome into the cell results in alteration of a property of the cell.

In certain embodiments of the compositions of the invention, the liposome further comprises an internalizing antibody or a fragment thereof attached to the exterior of the liposome, wherein the antibody or fragment binds to a specific cell surface antigen.

In another aspect, a method of delivering a nucleic acid to a cell is provided, the method comprising: contacting the cell with a composition comprising a liposome comprising an internalizing antibody or a fragment thereof attached to the exterior of the liposome, wherein the antibody or fragment binds to a specific cell surface antigen, and wherein the liposome with the internalizing antibody or a fragment thereof attached is internalized by a cell expressing at least 100,000 or at least 1,000,000 molecules of the antigen when contacted and incubated with the cell under internalizing conditions.

In still another aspect, a method of treating a patient in need thereof with a nucleic acid is provided, the method comprising administering to the patient an effective amount of a composition comprising a liposome comprising an internalizing antibody or a fragment thereof attached to the exterior of the liposome, wherein the antibody or fragment binds to a specific cell surface antigen, under conditions such that the patient is treated for a condition responsive to nucleic acid therapy.

In yet another aspect, a composition prepared by any of the methods described herein is provided, the composition comprising a liposome in an aqueous medium, wherein the liposome comprises: a nucleic acid; a polyamine; and a lipid component. In certain embodiments, the lipid component comprises a neutral phospholipid and no cationic lipid and wherein the nucleic acid and the lipid component are present at a ratio of from 5 nmol lipid per microgram of the nucleic acid to 20, 30, 40, 50, 60, 70, 80, 90, or 100 (optionally 5-20 or 30, preferably 10) nmol lipid per microgram of the nucleic acid, and wherein the liposome is from 30 to 500 nanometers in diameter.

In certain embodiments of the compositions described herein, the composition comprises no more than about 5 mol % or 1 mol % DOPE. In certain embodiments, the composition is essentially free of DOPE (e.g., has less than 0.1% DOPE by weight). In certain embodiments, transfection of the nucleic acid into the cell is at least about 10% more efficient (or at least about 20%, 30%, 40%, 50%, 60%, 70%, 80%, 90% or 100% more efficient) when DOPE is absent or, if present, is present at a concentration of no more than 5 mol. % of total lipid, compared to transfection of the nucleic acid into the cell with a composition identical except for the presence of cationic lipid at a concentration of more than 5 mol. % of total lipid; in certain embodiments, the transfection efficiency is transfection efficiency of a composition identical except for the presence of DOPE at a concentration of 10 mol. % of total lipid. In certain embodiments, the % dye accessibility of the composition is at least about 10% greater (or at least about 20%, 30%, 40%, 50%, 60%, 70%, 80%, 90% or 100% greater) when the DOPE is absent or, if present, is present at a concentration of no more than 5 mol. % of total lipid, compared to the % dye accessibility of a composition identical except for the presence of cationic lipid at a concentration of more than 5 mol. % of total lipid; in certain embodiments, the % dye accessibility is dye accessibility of a composition identical except for the presence of DOPE at a concentration of 10 mol. % of total lipid.

In certain embodiments, the liposome further comprises an internalizing antibody or a fragment thereof attached to the exterior of the liposome, wherein the antibody or fragment binds to a specific cell surface antigen.

BRIEF DESCRIPTION OF THE DRAWINGS

FIG. 3 shows the results of fluorescent microscopy of cells treated with liposomes (Her2 targeted and plain non-targeted) for 24 h. (1 sec exposure using Rh filter set). The values on the right indicate the theoretical charge, determined by taking the ratio of cationic lipid to DNA, and the % dye accessibility which indicates the % DNA entrapped within the liposome.

FIGS. 6A and 6B are (A) a chart showing entrapment analysis of liposomes containing a fixed amount of cationic lipid in the formulation to bind 10% of the available anionic phosphates charges in addition to varying amounts of spermine, and (B) a table displaying liposome size before and after sterile filtering through a 0.2 um PES filter and filtering efficiency.

FIGS. 7A and 7B are (A) a chart showing entrapment analysis of liposomes containing a fixed amount of cationic lipid in the formulation to bind 25% of the available anionic phosphates charges in addition to varying amounts of spermine, and (B) a table displaying liposome size before and after sterile filtering through a 0.2 um PES filter and filtering efficiency.

FIGS. 8A and 8B are (A) a chart showing entrapment analysis of liposomes containing a fixed amount of cationic lipid in the formulation to bind 50% of the available anionic phosphates charges in addition to varying amounts of spermine, and (B) a table displaying liposome size before and after sterile filtering through a 0.2 um PES filter and filtering efficiency.

DETAILED DESCRIPTION OF THE INVENTION

Figure 1A:
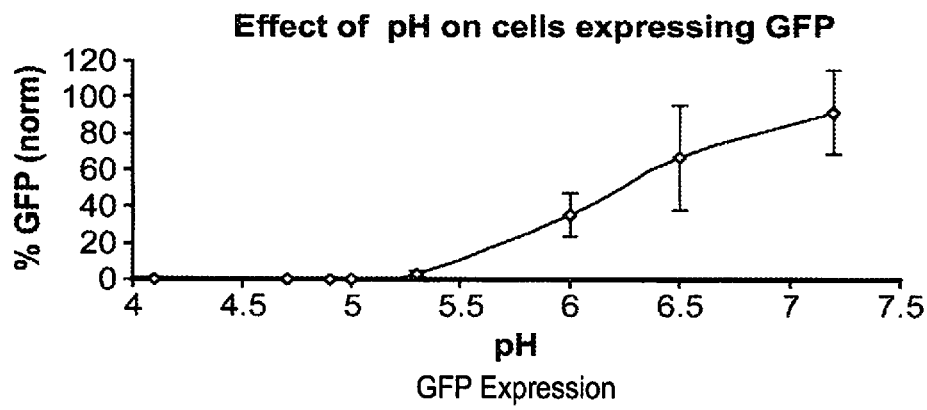
FIGS. 1A and 1B are graphs showing the effect of pH on GFP expression and luciferase expression, respectively.

It has now been found that improved liposomal compositions for the delivery of nucleic acids, in particular, DNA or RNA, can be prepared using organic-aqueous monophase assembly procedures, and/or incorporating polyamine or polymeric amine additives. In certain embodiments, the amount of cationic lipid used in the liposomal compositions reduced (compared to conventional cationic liposomes) or eliminated.

In certain embodiments, the nucleic acid is predissolved in an organic-aqueous monophase at neutral pH or higher and having relatively low buffering capacity, and the lipid and/or other liposome-forming component is dissolved in an organic-aqueous monophase at pH lower than neutral and having relatively higher buffering capacity, and the two solutions are combined at a temperature elevated above ambient, and quickly cooled down to temperature ambient or below, to avoid inactivation of the nucleic acid. It was unexpectedly found that exposure of DNA nucleic acid to pH below neutral (e.g., less than pH 6.5) in an aqueous-organic monophase, e.g., of 50 vol. % ethanol, can lead to the loss of transfection activity. However, shorter exposure times (1-2 min) and/or maintaining of the solution at higher pi (pH 6.5 or higher) preserves the transfection capacity of the DNA. For some RNAs, lower pHs may be preferable.

The present invention provides compositions for introducing a nucleic acid into a cell, the compositions comprising the nucleic acid in a complex with a polyamine or a polymeric amine, in a liposome also comprising lipids, wherein the lipids include a relatively low amount of a cationic lipid, or do not include a cationic lipid at all, and where the amount of the nucleic acid entrapped in the liposome is high, for example, 5-30 nmol lipid per microgram of the nucleic acid. In general, the compositions have no or very little transfection activity in the absence of ligand-directed targeting to cells, where, for example, the ligand is internalized by the cells, but have surprisingly high transfection activity when there is a cell-targeting ligand appended to the liposome surface, the transfection activity even exceeding that of the similar liposomes containing high levels (e.g., greater than 25% of total lipids) cationic lipid. Previously published methods to produce nucleic-acid carrying liposomes comprising non-cationic lipids, such as, phosphatidylcholines (PC) and cholesterol, with or without hydrophilic polymer-modified lipids, such as, PEG-phosphatidylethanolamine (PEG-PE), PEG-distearoylglycerol (PEG-DSG), or PEG-di($C_{12}$-$C_{15}$)alkylamine, (PEG being optionally methylated at the non-lipid-derivatized end) resulted in poor encapsulation efficiencies. The present inventors unexpectedly found that combining of a non-cationic lipid, such as dioleoyl-PC (DOPC) and cholesterol, optionally with PEG-DSG (PEG m.w. 2,000), and a nucleic acid in an organic-aqueous monophase, such as, for example, 50 vol. % aqueous ethanol, preferably at a temperature above ambient, for example, at 50-60° C., with subsequent cooling to the ambient temperature and removal of the ethanol by dialysis, results in a very efficient entrapment of the nucleic acid into small (<300 nm in size) liposomal particles, evidenced by decreased accessibility of the nucleic acid to a nucleic-acid-binding hydrophilic dye (20-30% accessibility, or at least 70%-80% DNA incorporated and protected from the dye). These liposomes did not transfect the nucleic acid into the cells, but when an internalizable, cell-specific ligand (e.g., an scFv antibody) was appended to the liposomes, they transfected the nucleic acid very effectively, as evidenced by the expression of the GFP transgene (see Examples 1-9, infra). The greater encapsulation efficiency in the absence of a cationic lipid is contrary to the conventional teaching of the art that states the need for a cationic lipid to impart affinity of the nucleic acid molecule for hydrophobic lipid phase and to ensure the solubility of the nucleic acid in the presence of an organic solvent, where the organic solvents are used to combine the nucleic acid and the lipid components of the liposomes. The increase of the hydrophilic polymer-conjugated lipid (e.g., PEG-DSPE) in the liposome, contrary to conventional belief, did not decrease the transfection efficiency of the ligand-targeted liposome, but rather, increased it; similarly, contrary to the conventional belief, the addition of a non-bilayer-forming, so-called "helper", lipid such as DOPE to the lipid composition of the liposomes did not increase the effectiveness of transfection. Spermine, spermidine, short (n=4-5) oligomeric ethyleneimines, and both linear and branched polyethyeneimines (M.W. 400-1800) were tested and found suitable for preparing the inventive liposomes. The range of non-precipitating ratios of the polyamine or polymeric amine to the nucleic acid in the organic-aqueous monophase can be determined by turbidimetric titration.

In certain embodiments, a suitable ratio of positive charge (polyamine or polymeric amine) to negative charge (nucleic acid phosphate groups) is about 0.9:1 or about 1:1. In the absence of polyamine or polymeric amine, the nucleic acid was quite poorly encapsulated in the liposomes after mixing in an organo-aqueous monophase and removal of the organic solvent (dye accessibility about 80-90%). When the DNA was combined with a polymeric amine or a polyamine, as indicated above, and when the amount of a cationic lipid was reduced, or when a cationic lipid was a single hydrocarbon-chain lipid, or when the cationic lipid was completely omitted from the composition, the DNA was incorporated into the liposomes of DOPC and cholesterol very effectively (see Examples 1-9, infra). The particles had small size, near the volume-weighed average of 200 nm, and when delivered via appended cell-internalizing ligand to the cancer cells in vitro, the distribution of the liposome material, according to the fluorescent microscopy data, was more diffuse and uniform than the distribution of similarly prepared liposomes containing cationic lipids, which was more punctate and appeared to concentrate in discrete subcellular compartments. This observation was in agreement with more effective transgene (GFP) expression of the delivered plasmid DNA in these cells by the inventive liposomes, compared to those containing cationic lipids in usual amounts (i.e., about 0.5 to 2.0 positive-to-negative (DNA) charge ratio). For example, the liposomes of non-cationic lipids and polyamine/polymeric amine-nucleic acid formed effectively when the components were combined in 50 vol. % ethanol-low ionic aqueous buffer at pH 7.0-7.5, at 50-60° C., by mixing the solutions of the lipid component and the DNA-polyamine/polymeric amine component, followed by cooling and removal of ethanol, e.g. by dialysis against a neutral aqueous buffer at physiological concentration of sodium chloride. It was unexpectedly found that this process, albeit not including a "high-transition temperature" lipid component, gave better results if the components were combined at the elevated (50-60° C.), rather than ambient, temperature. Additionally, we found that the presence of sterol (cholesterol) was helpful to obtain effective dissolution of DOPC component in the 50 vol. % ethanol-organic phase, which is surprising over the fact that cholesterol itself is poorly soluble in an aqueous-organic monophase of this kind.

Definitions

The term "cationic lipid", as used herein, is art-recognized and refers to lipid moieties having a net positive charge. Examples of cationic lipids include dioleyl-N,N-dimethyl-ammonium chloride ("DODAC"); N-(2,3-dioleyloxy)propyl)-N,N,N-trimethylammonium chloride ("DOTMA"); N,N-distearyl-N,N-dimethylammonium bromide ("DDAB"); N-(2,3-dioleyloxy)propyl)-N,N,N-trimethylammonium chloride ("DOTAP"); 3β-(N—(N',N'-dimethylaminoethane)-carbamoyl)cholesterol ("DC-Chol"); N-(1,2-dimyristyloxyprop-3-yl)-N,N-dimethyl-N-hydroxyethyl ammonium bromide ("DMRIE"); N-(1-(2,3-dioleyloxy)propyl)-N-(2-(sperminecarboxamido)ethyl)-N,N-dimethylammonium trifluoroacetate ("DOSPA"); dioctadecylamidoglycyl carboxyspermine ("DOGS"); N-(2,3-dioleyloxy)propyl)-N,N-dimethylammonium chloride ("DODMA"); 1,2-dioleoyl-sn-3-glycero(ethylphosphoryl)-choline ("DOEPC"); 1,2-dimyristoyl-sn-3-glycero(ethylphosphoryl)-choline ("DMEPC"); 1-palmitoyl-2-oleoyl-3-glycero(ethylphosphoryl)-choline ("POEPC"); 1,2-distearoyl-3-glycero(ethylphosphoryl)-choline ("DSEPC"); N-agrinyl-1,2-dioleoylphosphatidylethanolamone ("Arg-DOPE"); and 1,2-Dioleoyl-3-dimethylammonium-propane ("DODAP").

The term "neutral lipid", as used herein, is art-recognized and refers to lipid moieties having no net charge. A neutral lipid may have no charge, or may be zwitterionic. Examples of neutral lipids include 1,2-dioleoyl-sn-3-phosphoethanolamine ("DOPE"); 1,2-dioleoyl-sn-glycero-3-phosphocholine ("DOPC"); polyethylene glycol-distearoylglycerol ("PEG-DSG"); 1,2-dioleoyl-sn-glycero-3-ethylphosphocholine ("EPC"); 1-palmitoyl-2-oleoyl-sn-glycero-3-phosphocholine ("POPC"); and sterols such as cholesterol.

The term "liposome" as used herein refers to conventional liposomes (having an aqueous phase in the interior) as well as to nanoparticles having a lower internal water content.

A nucleic acid useful in embodiments of the present invention is selected according to the biological or physiological effect desired to be produced, e.g. by its delivery into living cells. Such selection is well known to the skilled artisans in the fields of molecular biology and medicine. A nucleic acid is a polymeric material that is a nucleic acid or resembles in its structure and function a nucleic acid in that it exhibits a backbone of covalently linked repetitive molecular units (also referred to as monomers) and has a biological or physiological effect. A nucleic acid may include natural, modified or synthetic bases and backbone elements. A nucleic acid may be of natural or synthetic origin and may include a nucleic acid (i.e., a polymer that comprises a plurality of nucleic acid bases attached to a backbone of covalently linked repetitive molecular units), DNA, RNA, natural and synthetic oligonucleotides (including antisense oligonucleotides, interfering RNA, small interfering RNA (siRNA), small hairpin RNA (shRNA)), double-stranded RNAs that are about 30 base pairs in length and can act as dicer enzyme substrates, nucleoprotein, peptide, nucleic acid, ribozyme, DNA-containing nucleoprotein, such as an intact or partially deproteinated viral particles (virions), oligomeric and polymeric anionic compounds other than DNA (for example, acid polysaccharides and glycoproteins), and the like. It is preferably DNA or RNA, and is more preferably DNA carrying a sequence of an expressible gene or siRNA. Antisense oligonucleotides are another preferred type of nucleic acids. To signify the process of transfer of an exogenous nucleic acid into a living cell we will use the term "transfection" without limitation to any particular kind of nucleic acid or to any particular function that may be performed in the cell by a nucleic acid so transferred. The transfection may be performed on cells in the body of a subject to be treated (in vivo) or on cells maintained outside a subject (in vitro or ex vivo). The terms "transfection" and "delivery" will be used interchangeably in this description. When it is advantageous for a particular application, liposomes may contain more than one kind of nucleic acid in respect to structure, function, or nucleotide sequences.

A "polyamine" or "polymeric amine", as used herein, is a non-lipid compound having multiple (at least two) basic nitrogen moieties capable of having a positive charge. Polyamines include linear, branched, or cyclic compounds having from 2 to 20 amino groups. In certain embodiments, a polyamine has a molecular weight of not more than about 2000 daltons, or not more than about 1800 daltons, or not more than about 600 daltons, or not more than about 400, 300, or 250 daltons. In certain embodiments, the polyamine has no more than twenty carbon atoms in total. Examples of polyamines include spermine, spermidine, putrescine, and polyamino$C_2$-$C_{10}$alkanes (such as a $\alpha,\omega$-amino$C_2$-$C_{10}$alkane), in which the aliphatic chain can be interrupted by one or two nitrogen atoms. In certain embodiments, the polyamine is spermine. Polymeric amines include compounds such as oligoethyleneimine, polyethyleneimine, and the like.

Compositions and Methods of Making the Compositions

In general, the compositions provided herein are prepared by providing a first solution containing the nucleic acid and a second solution containing the lipid component, mixing the two solutions together under suitable conditions so that a liposome is prepared.

In certain embodiments, one or both of the first and second solutions comprises a water-miscible organic solvent. The water-miscible organic solvent generally maintains complete miscibility with water (single liquid phase or monophase) under the conditions chosen for the lipid component-nucleic acid combining and organic solvent amount reducing steps described below, i.e., over the entire range from about 0.01 vol. % up to about 60 vol. %.

The water-miscible organic solvent of this step is preferably an alcohol, or an aprotic solvent, and is preferably one suitable for use in biological preparation. Examples of the alcohol solvent include methanol, ethanol, 1-propanol, 2-propanol, 2-butanol, tert-butanol, ethylene glycol, diethylene glycol, propylene glycol, glycerol, methylcellosolve (ethylene glycol monomethyl ether), methylcarbitol (diethylene glycol monomethyl ether) and the like. Methanol, ethanol or tert-butanol are preferred, particularly ethanol. Aprotic solvents include an ether, an ester, a ketone, a nitrile, an amide, or a sulfoxide. The aprotic solvent is preferably ethylene glycol dimethyl ether, ethylene glycol diethyl ether, diethyleneglycol dimethyl ether, dioxane, tetrahydrofurane, acetone, methylethylketone, acetonitrile, dimethylformamide, or dimethylsulfoxide.

A lipid component solution can be combined with a nucleic acid solution under conditions that are sufficient to form the desired microparticulate complex. The selected nucleic acid is combined with the lipid component in a solution having a single liquid phase (i.e., monophasic) comprising water and water-miscible organic solvent selected as described above. The monophasic composition is a mixture characterized by the absence of liquid-liquid interfaces, without regard to its optical clarity, as discussed below. The lipid component and nucleic acid can be combined using any method known in the art. The percentage of the organic solvent by volume present in the resulting aqueous/organic solvent mixture will vary according to the type of nucleic acid and lipid component used in the process. This percentage may range from about 10% vol. to about 60% vol., generally up to about 55% volume. The temperature range at which the process takes place is above the freezing point of the aqueous/organic solvent mixture, but below the boiling point of the organic solvent; it will typically vary from about 0° C., to no more than 100° C. under ambient conditions of pressure. Temperatures above ambient, such as in the range of 30° C. to 70° C., are preferred, especially about 40° to about 65° C. In general, the temperature can be higher for longer, more stable nucleic acids; conversely, the temperature can be lower for shorter, less stable oligonucleotides such as siRNA or shRNA, to reduce denaturation of the oligonucleotide duplex.

One preferred method is to prepare a solution of the nucleic acid in an essentially aqueous medium, prepare the lipid component as a solution in the organic solvent, and combine the two solutions, for example by mechanical mixing, in the volume ratio providing in the mixture the necessary content of the organic solvent. The content of the organic solvent in the resulting mixture preferably provides for partial dehydration and/or condensation of the nucleic acid, while keeping the nucleic acid in a dissolved state; and at the same time, the organic content solubilizes the lipid component into a non-vesicular form, such as, for example, micellar form.

Another preferred method is to prepare the nucleic acid solution in a single fluid phase containing water and a first volume percentage of the water-miscible organic solvent, prepare the lipid component solution in a single fluid phase containing water and a second volume percentage of the water-miscible organic solvent, and combine these two solutions, for example by mechanical mixing, in the volume ratio providing in the mixture the necessary content of the organic solvent as specified below. The first and second volume percentages of the organic solvent in these two solutions are preferably the same. The volume percentage of the organic solvent in the first (nucleic acid) solution is preferably chosen to facilitate the transition e.g., of the nucleic acid molecule into condensed and/or less hydrated, form, while the volume percentage of the organic solvent in the second (lipid component) solution solubilizes, e.g., a lipid into a non-vesicular, such as micellar, form. Thus a skilled artisan would choose the content of the organic solvent in the nucleic acid and lipid solutions, as well as in the resulting mixture, to satisfy both the need to facilitate nucleic acid dehydration and/or condensation, and the need for lipid solubilization.

According to the third preferred method, a lipid component is provided in the neat form, preferably in the form having high surface area, such as a film deposited on an insoluble substrate, and then contacted with the nucleic acid solution in a single fluid phase containing water and water-miscible organic solvent in the volume percentage to satisfy the need for nucleic acid dehydratation/condensation and/or lipid component solubilization, which percentage is more particularly defined below. Contacting of the neat lipid component with the nucleic acid solution is preferably accompanied by mechanical agitation, such as slow rotation or reciprocation of the vessel in which the contacting is conducted, so that the lipid component is solubilized and contacts the nucleic acid, preferably in a condensed state, to ensure formation of the microparticulate complex. The agitation typically continues until essentially all of the neat lipid component is solubilized.

The organic solvent in the resulting nucleic acid/lipid component solution is preferably present at the volume concentration at which both the nucleic acid, such as nucleic acid, and the lipid component are independently molecularly or micellarly soluble. That is, the organic-aqueous monophase produced after combining the nucleic acid with the lipid component would be able to dissolve either the nucleic acid or the lipid component in the form of a molecular or micellar solution without the need of both nucleic acid and lipid component to be present during the dissolution. Preferably, when the content of the organic solvent, and/or the temperature at which nucleic acid and lipid component are combined, is decreased, the lipid component forms a self-assembled, non-micellar, condensed phase, such as bilayer, inverted hexagonal, cubic, liquid crystalline, or amorphous phase. A lipid component that in aqueous environment form ordered condensed phases, such as bilayers, cubic, or inverted hexagonal phases, known as lyotropic liquid crystals, are particularly preferred. Such lipid components are known in the art. Bilayer-forming lipid components in aqueous environment typically form enclosed structures, such as vesicles. Preferentially, the ability of the lipid component to form a self-assembled, condensed phase upon reduction of the organic solvent concentration in the monophase is independent of whether or not a nucleic acid is present. Exemplary classes of lipid component that form self-assembled, non-micellar, condensed phases in aqueous environment are known in the art and can be selected by one of ordinary skill in the art using no more than routine experimentation. These exemplary lipid components are designated as Class I insoluble, non-swelling amphiphiles (spread on interface to form stable monolayer: water-insoluble or having very low solubility) and Class II—insoluble, swelling amphiphiles (spread to form stable monolayer at interface and are insoluble but swell in water to form lyotropic liquid crystals). Particular examples of lipid components are disclosed herein.

The particular concentration of the organic solvent selected for any given mixture would depend on the nature of the organic solvent, the lipid component, and the nucleic acid; the temperature at which the components are combined; the ionic strength of the aqueous component; and the concentration of lipid component and/or nucleic acid in the mixture. Once the organic solvent, the nucleic acid, the aqueous component, and the lipid component are selected according to the needs of a particular application, a skilled artisan being guided by this specification, would easily establish the required concentration of the organic solvent by performing simple solubility tests known in the art. For example, the molecular or micellar nature of the dissolved nucleic acid and/or lipid can be determined by dynamic light scattering. Light scattering intensity can be used as well, since micellar or especially molecular (true) solutions have substantially lower light scattering than those containing particles, vesicles, filaments, or other elements comprising aggregated nucleic acid or lipid component phases. Other methods know in the art, such as NMR, ESR probe, and fluorescent probe methods can be used to detect the presence of nucleic acid or lipid component in the state other than micellar or molecular solution.

The amount of an organic solvent in the mixture is so elected as to provide for nucleic acid and lipid component to be independently micellarly or molecularly soluble in the resulting aqueous-organic solvent monophase. Typically this amount is from about 10 vol. % to about 60 vol. %, preferably from 30 vol. % to 55 vol. %, and most preferably from about 45 vol. % to about 55 vol. %.

The lipid component can comprise neutral or cationic lipids. In a preferred embodiment, the amount of cationic lipid is present at a concentration of no more than 5 mol. % of total lipid (optionally no more than 4 mol. %, 3 mol. %, 2 mol. %, 1 mol. %, or 0.5 mol. % of total lipid, or essentially free of cationic lipid). Any particular amount of non-cationic lipids will depend on the nature of this lipid, the chosen cationic lipid, the nucleic acid, and the organic solvent. Sterols may be present in the amount of up to 100% of the non-cationic lipid. If phospholipids, such as for example, phosphatidylcholine, are present, sterols, such as for example, cholesterol, may constitute up to 50 mol. % of the non-cationic lipid. The nucleic acid solution and the lipid, whether in solution or in a neat form, are preferably combined at the temperature above ambient and above the highest of the phase transition temperatures of the lipids present in the solution, but below the boiling point of the organic solvent, more preferably between about 30° C. and about 80° C., yet more preferably between about 40° C. and about 70° C., and optimally between about 50° C. and 65° C. The precise temperature at which the nucleic acid and lipid component are combined also provides for molecular or micellar dissolution of both components in the chosen monophase. This temperature can be determined, for example, by the solubility tests described above.

Aqueous component of the fluid phase is preferably of low ionic strength, i.e., at or below the physiological value (that of 144 mM NaCl), more preferably below that of 50 mM NaCl, and most preferably less than that of 10 mM NaCl. Ionic strength is defined as one-half the sum of concentrations of all ions in a solution multiplied by the square of their ionic charges. Without being limited by a particular theory, it is believed that low ionic strength at the lipid component/nucleic acid combining step reduces the risk of liposome aggregation and precipitation and eliminates the requirement of sterically stabilizing lipid components to be present during this step. The aqueous component may also contain buffer substances to maintain the desired pH, typically in the range from about 3.0 to about 10.0, more preferably in the physiological pH from about 4.0 to about 9.0. In certain embodiments, the pH is between about 5.5 and about 6.5. The amount of the buffer substance is chosen to keep the ionic strength low, within the above range of ionic strength.

In preferred embodiments, the polyamine or polymeric amine is added to the solution of the nucleic acid prior to mixing of the nucleic acid solution with the lipid component solution.

After combining the nucleic acid and lipid component, the amount of the organic solvent in the mixture is reduced to effect formation of liposomes. It is believed that reduction of the organic solvent contents promotes lipid bilayer formation around the condensed nucleic acid/lipid core, this effecting the formation and stabilization of liposomes. Thus, the amount of organic solvent is preferentially reduced to the point of self-assembly of the nucleic acid/lipid complex into particles. If, as evidenced, for example, by particle size measurements, the formation of nucleic acid/lipid particles occurs at the monophase step, removal of organic solvent is optional, and may serve the purpose of, for example, improving biocompatibility of the transfecting formulation. The amount of organic solvent is preferably reduced to, or below, the point where bilayer formation is achieved. Generally, this amount is less than about 20 vol. %. Most preferably, essentially all of the organic solvent is removed, e.g. down to about 0.01 vol. %; however in some topical applications, such as the nucleic acid delivery to the cells of skin, it is advantageous to a pharmaceutically acceptable organic solvent and retain a percentage of the solvent (e.g. ethanol) in the composition. Reduction of the organic solvent is achieved by any means available in the art, such as, for example, by dialysis, gel-chromatography, absorption, evaporation under reduced pressure, ultrafiltration, size-exclusion chromatography, lyophilization, or a combination thereof. It also enables the liposomes to be transferred into appropriate medium for storage or final use. Prior to, or in the course of, the reduction of the organic solvent content in the mixture, the ionic strength of the medium can be brought up to physiological value (that of 144 mM NaCl), for example, by addition of the concentrated salt solution, followed by mixing. It was unexpectedly found that the liposomes remain stable against aggregation in physiological salt solutions even in the absence of aggregation-preventing polymer-lipid conjugates.

The temperature at which the organic solvent is removed is preferably the one at which the nucleic acid was combined with the lipid component. However the temperature can be first brought to ambient or below up to refrigeration temperature of 4-8° C. The latter is more suitable when low phase transition temperature lipids, such as the ones containing unsaturated fatty acid chains (phase transition temperature<4° C.), are used.

In certain embodiments, liposomes provided herein have reduced water content compared to conventional liposomes. See, e.g., U.S. Patent Application Publication No. 2007/0171077, the contents of which are incorporated herein by reference, for discussion of certain compositions having reduced water content and methods of making such compositions. The lipid shell surrounds the nucleic-acid-containing core closely so that between the core and the shell there is little space holding extraneous small molecules (solutes). Typically, the aqueous content of the inner space enclosed by the shell is less than 50%, and more preferably, 20% or less of that calculated from the particle size. The latter value corresponds to the expected amount of water immobilized in the hydration layer of the nucleic acid contained within the particle. Thus, liposomes of these embodiments in an aqueous medium may contain encapsulated water in the amount approximating the hydration water immobilized by the encapsulated nucleic acid. In certain embodiments, the liposome contains encapsulated water in the amount approximating the hydration water immobilized by the encapsulated nucleic acid. In certain embodiments, the liposome has an interior having an enclosed interior volume containing the nucleic acid in a condensed state and the enclosed interior has an aqueous content of less than about 50% of the volume, as calculated from liposome particle size, or alternately, the aqueous content is 20% of the volume or less.

A liposome as provided herein also optionally contains associated therewith a ligand that facilitates the liposome's entry into a cell, i.e., a cell-specific ligand. The ligand is a chemical moiety, such as a molecule, a functional group, or fragment thereof, which is specifically reactive with the cell of choice while being less reactive with other cells thus giving the liposome an advantage of transferring nucleic acids, selectively into the cells of choice. By being "reactive" it is meant having binding affinity to a cell or tissue, or being capable of internalizing into a cell wherein binding affinity is detectable by any means known in the art, for example, by any standard in vitro assay such as ELISA, flow cytometry, immunocytochemistry, surface plasmon resonance, etc. Usually a ligand binds to a particular molecular moiety—an epitope, such as a molecule, a functional group, or a molecular complex associated with a cell or tissue, forming a binding pair of two members. It is recognized that in a binding pair, any member may be a ligand, while the other being an epitope. Such binding pairs are known in the art. Exemplary binding pairs are antibody-antigen, hormone-receptor, enzyme-substrate, nutrient (e.g. vitamin)-transport protein, growth factor-growth factor receptor, carbohydrate-lectin, and two polynucleotides having complementary sequences. Fragments of the ligands are to be considered a ligand and may be used so long as the fragment retains the ability to bind to the appropriate cell surface epitope. Preferably, the ligands are proteins and peptides comprising antigen-binding sequences of an immunoglobulin. More preferably, the ligands are antigen-binding antibody fragments lacking Fc sequences. Such preferred ligands are Fab fragments of an immunoglobulin, $F(ab)_2$ fragments of immunoglobulin, Fv antibody fragments, or single-chain Fv antibody fragments. These fragments can be enzymatically derived or produced recombinantly. In their functional aspect, the ligands are preferably internalizable ligands, i.e., the ligands that are internalized by the cell of choice for example, by the process of endocytosis. Likewise, ligands with substitutions or other alterations, but which retain the epitope binding ability, may be used. The ligands are advantageously selected to recognize pathological cells, for example, malignant cells or infectious agents. Ligands that bind to cell surface epitopes are preferred. One especially preferred group of ligands are those that form a binding pair with the tyrosine kinase growth factor receptors which are overexpressed on the cell surfaces in many tumors. Exemplary tyrosine kinase growth factors are the VEGF receptor, FGF receptor, PDGF receptor, IGF receptor, EGF receptor, TGF-alpha receptor, TGF-beta receptor, HB-EGF receptor, ErbB2 receptor, ErbB3 receptor, and ErbB4 receptor. EGF receptor vIII and ErbB2 (HER2) receptors are especially preferred in the context of cancer treatment using liposomes as these receptors are more specific to malignant cells, while scarce on normal ones. Alternatively, the ligands are selected to recognize the cells in need of genetic correction, or genetic alteration by introduction of a beneficial gene, such as: liver cells, epithelial cells, endocrine cells in genetically deficient organisms, in vitro embryonic cells, germ cells, stem cells, reproductive cells, hybrid cells, plant cells, or any cells used in an industrial process.

The ligand may be attached to the liposome by any suitable method available in the art. The attachment may be covalent or non-covalent, such as by adsorption or complex formation. The attachment preferably involves a lipophilic molecular moiety capable of conjugating to the ligand by forming a covalent or non-covalent bond, and referred to as an "anchor". An anchor has affinity to lipophilic environments such as lipid micelles, bilayers, and other condensed phases, and thereby attaches the ligand to a lipid-nucleic acid microparticle. Methods of the ligand attachment via a lipophilic anchor are known in the art. Typically, an amount of a lipophilic anchor effective to provide ligand conjugation is included into the lipid component, e.g. lipid, prior to, or during, the liposome formation. Alternatively, the conjugate of an anchor and a ligand can be first formed, and then incorporated into liposomes by addition to the lipid prior to the liposome formation, or by addition of the conjugate to the aqueous suspension of liposomes after their formation. A particularly suitable mode of ligand attachment to liposomes is by using a ligand conjugated to a lipophilic anchor through an intermediate hydrophilic polymer linker. Thus, the ligand moves freely above the microparticle surface and can react even with hard-to-reach epitopes on the cell surface. Ligands conjugated to lipophilic anchors via a hydrophilic polymer intermediate linker advantageously become stably associated with preformed nucleic acid-lipid liposomes during co-incubation of the conjugated ligands and the liposomes in an aqueous medium. (U.S. Pat. No. 6,210,707, the contents of which are incorporated herein by reference). For additional discussion of targeting moieties and their incorporation into liposomes, see, e.g., U.S. Pat. No. 7,244,826; U.S. Pat. No. 7,507,407; and U.S. Pat. No. 6,794,128; the contents of each of these patents are incorporated herein by reference.

The liposomes can further comprise other components beneficial for its function of transfecting cells. These can be viewed as transfection-enhancing components, i.e., an entity associated with the liposome that improves the delivery of an exogenous nucleic acid to a living cell. These beneficial, transfection-enhancing components, may include, without limitation, endosome-escape agents, nuclear localization factors, triggerable means for enhanced transfer into cytosol, pH-sensitive compounds, heat and radiation-triggerable release, and membrane fusion promoters such as membrane fusion-enhancing or membrane fusion-inducing compounds, intracellular nucleic acid release-enhancing or inducing components, transcription factors, and promoter-modulating compounds.

In certain preferred embodiments, the liposomes provided herein are capable of entrapping high percentages of the nucleic acid in the nucleic acid solution. For example, in preferred embodiments, at least 5%, 10%, 20%, 30%, 40%, 50%, 60%, 70%, 75% 80%, 85% or 90% of the nucleic acid present in the nucleic acid solution (prior to mixing with the lipid component solution) is entrapped within the liposomes. The extent of trapping of the nucleic acid can be measured using assays such as the assays described in the Examples herein.

In certain preferred embodiments, the ratio of lipid to nucleic acid is of from 1 nanomole (nmol) lipid per microgram of the nucleic acid to 20, 30, 40, 50, 60, 70, 80, 90, or 100 (optionally 2.5-20 or 30, preferably 10, or 5-20, or 5-10) nmol lipid per microgram of the nucleic acid. It has now been found that entrapment of the nucleic acid is more efficient when the ratio of lipid to nucleic acid is at least 2.5 nmol lipid per microgram of the nucleic acid.

In certain embodiments, the liposome is from 30 to 500 nanometers (nm) in diameter. In other embodiments, the liposome is from about 40 to about 250 nm, or from about 40 to about 200 nm in diameter.

Pharmaceutical Compositions

Pharmaceutical compositions comprising the liposomes provided herein are prepared according to standard techniques and further comprise a pharmaceutically acceptable carrier. Generally, normal saline will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. These compositions may be sterilized by conventional, well known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. Additionally, the liposome suspension may include lipid-protective agents which protect lipids against free-radical and lipid-peroxidative damages on storage. Lipophilic free-radical quenchers, such as alphatocopherol and water-soluble iron-specific chelators, such as ferrioxamine, are suitable.

The concentration of liposomes in pharmaceutical formulations can vary widely, i.e., from less than about 0.05%, usually at or at least about 2-5% to as much as 10 to 30% by weight and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. The amount of liposome administered will depend upon the particular lipids and targeting ligands used, the disease state being treated, the therapeutic agent being delivered, and the judgment of the clinician. Generally the amount of liposomes administered will be sufficient to deliver a therapeutically effective dose of the particular nucleic acid. The quantity of liposomes necessary to deliver a therapeutically effective dose can be determined by uptake assays as described above along with consideration of the condition to be treated. For example, immunoliposome dosages may be between about 0.01 and about 50 mg per kilogram of body weight, or between about 0.1 and about 10 mg/kg of body weight.

Preferably, the pharmaceutical compositions are administered parenterally, i.e., intraarticularly, intravenously, intraperitoneally, subcutaneously, by direct injection into the brain (intrathecally or via convection enhanced delivery) or intramuscularly. In certain embodiments the pharmaceutical compositions are administered intravenously or intraperitoneally by a bolus injection. Particular formulations which are suitable for this use are well known in the art. Typically, the formulations will comprise a solution of the liposomes suspended in an acceptable carrier, preferably an aqueous carrier. A variety of aqueous carriers may be used, e.g., water, buffered water, 0.9% isotonic saline, and the like. These compositions may be sterilized, e.g., by filtration. The resulting aqueous solutions may be packaged for use as is. In certain instances the solutions can be frozen. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

In certain embodiments, the nanoparticles (liposomes) provided herein can be used to treat any of the cancers disclosed in U.S. Pat. No. 7,846,440, the contents of which are incorporated herein by reference. In addition, the nanoparticles (liposomes) can used for cancer treatment in conjunction with one or more anti-cancer agents disclosed in U.S. Pat. No. 7,846,440 (e.g., as disclosed in the Table of anti-cancer agents spanning Col. 19-Col. 24 of U.S. Pat. No. 7,846,440).

The following examples are provided by way of illustration and not limitation.

EXAMPLES

Example 1: Lipid Formulation with Added Polyamine

Abbreviations

GFP: Green fluorescent protein
MES: 2-(N-morpholino)ethanesulfonic acid
TE buffer: Tris/EDTA buffer
HBS: HEPES buffer
PEI: polyethyleneimine
Hank's BSS: Hank's balanced salt solution
DOTAP: dioleoyl trimethylammonium propane
DOPC: 1,2-dioleoyl-sn-glycero-3-phosphocholine
Chol: cholesterol
DOPE: 1,2-dioleoyl-sn-glycero-3-phosphoethanolamine
CHEMS: cholesteryl hemisuccinate
PEG: polyethylene glycol
PEG-DSG: PEG-distearoylglycerol
DOSPA: N-(1-(2,3-dioleyloxy)propyl)-N-(2-(sperminecarboxamido)ethyl)-N,N-dimethyl-ammonium trifluoroacetate
CHIM: cholesterol imidazole derivative
DiI(3)-DS: a cationic lipid dye:

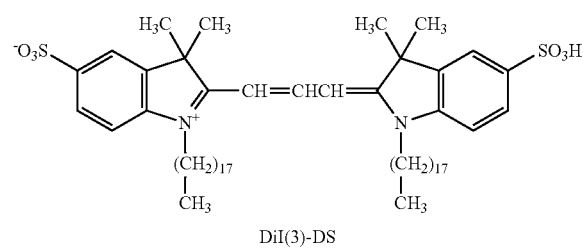

DiI(3)-DS

Liposome Preparation

The polyamine was mixed with GFP plasmid DNA in 50% ethanol/50% 20 mM MES, pH 5.1. The lipid mixtures were dissolved in 50% ethanol/50% 2 mM TE buffer, pH 8.0. The polyamine mixture and the lipid mixture were heated at 60° C. for 2 minutes, mixed, and allowed to cool to room temperature with stirring. The mixture was transferred to a dialysis cassette (MWCO 10,000) and dialysed against saline (×2) and then HBS, pH 7.25. After 4 h total dialysis time, samples were removed and tested for DNA concentration, dye accessibility and size. Picogreen® dye accessibility assay was performed as described in Example 12, infra.

PEI MW 600, PEI MW 1800 and Spermine were used as the polyamine molecules. Two ratios of PEI (Nitrogen) to DNA (Phosphate) were used, N/P=1.33 and 0.67. At N/P=1.33 DNA undergoes aggregation in 50% ethanol mixtures, observed by the appearance of turbidity.

The samples were immunotargeted by the addition of an antiHer2-lipid conjugate, and the GFP transfection measured. Samples were prepared as above and targeted (T) by addition of 15 μg/μmol PC of F5-PEG-DSPE antibody-lipid conjugate by an insertion methodology described, e.g., in U.S. Pat. No. 6,210,707. Non-targeted (NT) particles are those particles to which no antibody conjugate has been added.

SKBR3 cells (ATCC® #HTB-30™, grown in McCoy's 5A media with 10% FBS) were plated at a density of 100,000 cells/well in a 24 well plate the day previously. DNA was mixed with Lipofectamine™ 2000 as described by the manufacturer's instructions, and 1 μg DNA per well was added to the cells. 1 μg of encapsulated DNA, and free DNA was also added to each well (in duplicate). After 24 h, the cells were washed and 1 mL media added. After a further 24 h, the cells were assayed for the green fluorescent protein (GFP). This entailed being washed twice with Hank's BSS solution and viewed under a fluorescence microscope for GFP positive cells. GFP expression is calculated as the number of fluorescent cells/total number of cells×100 over many fields of view (n>3).

Lipid Formulations

Lipid amounts are shown as DOTAP/DOPC/Chol/DOPE/CHEMS/CHIM/DiI(3)-DS.
Formulation 1: as above in the ratios 6/20/7/5/6/3.67/0.47/0.05 nmol per 1 μg DNA
Formulation 2: as above in the ratios 3/16/4/15/5/0.225/0.045 nmol per 1 μg DNA with PEI 600 added to DNA at a N/P=1.33
Formulation 3: as above in the ratios 3/16/4/15/5/0.225/0.045 nmol per 1 μg DNA with PEI 1800 added to DNA at N/P=1.33
Formulation 4: as above in the ratios 3/16/4/15/5/0.225/0.045 nmol per 1 μg DNA with Spermine added to DNA at N/P=1.33
Formulation 5: as above in the ratios 3/16/4/15/5/0.225/0.045 nmol per 1 μg DNA with PEI 600 added to DNA at N/P=0.67
Formulation 6: as above in the ratios 3/16/4/15/5/0.225/0.045 nmol per 1 μg DNA with PEI 1800 added to DNA at N/P=0.67
Formulation 7: as above in the ratios 3/16/4/15/5/0.225/0.045 nmol per 1 μg DNA with Spermine added to DNA at N/P=0.67
Formulation 8: lipid formulation of DOTAP/DOPC/Chol/PEG-DSG/DiI(3)-DS (0.3/15/10/0.3/0.03) nmol per 1 μg DNA with Spermine added to DNA at N/P=0.9

Results

| Formulation # | Size nm ± nm | % Dye Accessibility |
|---|---|---|
| 1 | 114.7 ± 50.4 | 21.4 ± 1.2 |
| 2 | 149.3 ± 46.2 | 35.0 ± 1.0 |
| 3 | 147.8 ± 49.1 | 26.5 ± 0.8 |
| 4 | 155.6 ± 31.8 | 45.1 ± 1.9 |
| 5 | 126.3 ± 54.0 | 24.4 ± 1.1 |
| 6 | 115.4 ± 51.2 | 23.3 ± 1.1 |
| 7 | 126.1 ± 45.3 | 35.8 ± 1.9 |
| 8 | 166.1 ± 72.8 | 35.9 ± 3.8 |

Observed Gene Expression Results

After 24 h, it was evident that the targeted liposomes were internalized to a large extent, while the non-targeted liposomes were not. This was judged by the DiI(3)-DS fluorescence, which was used as a lipid marker. However, only the Lipofectamine™ 2000 samples exhibit any GFP signal. At 48 h, the targeted versions of #3, 5 and 6 gave higher GFP signal than the targeted versions of 1, 2, 4 or 7. However, the targeted sample 8 gave approximately twice the levels of GFP than any of the other liposomes. In all cases non-targeted samples had no GFP signal. Lipofectamine™ 2000 gave the highest GFP signal at 48 h.

Conclusion

Polyamines can be successfully incorporated into liposomes without causing extensive aggregation of the particles. However, it is noticeable that the liposomes were more susceptible to dye accessibility and the liposomes were a little larger. It is unknown at this point, whether the increase in dye accessibility is due to incomplete DNA entrapment or the liposomes give reduced protection to the encapsulated DNA.

It was surprising that formulation 8 gave DNA protection at all; this formulation gave the highest GFP signal of any of the samples in the transfection assay. The amount of cationic lipid present in this formulation (+/−=0.1) is well below the quantity expected (based on the prior art) to bind DNA in such a way to form cationic liposomes. Cationic liposomes using the formulation DOTAP/POPC/Chol do not form properly (they aggregate during dialysis) at +/−<1.67.

Example 2: Method

DNA (100 μg) was prepared in a 50% ethanol solution as described above. From a stock solution of PEI 600, aliquots were added to in such volumes to give N/P=0, 0.67, 1.33 and 4. Separately, a solution of 2 mM TE buffer, pH 8.0 and ethanol (50% v/v) were prepared. The solution were heated at 60° C. for 2 min and mixed. The samples were cooled and dialysed as above. DNA concentration and dye accessibility was measured as above.
Results

| Sample | plate1 [dna]ng/ml | stdev | plate2 [dna]ng/ml | stdev | % Dye Acces | stdev | [DNA]ug/ml | stdev |
|---|---|---|---|---|---|---|---|---|
| naked DNA | 729.11 | 6.8 | 779.12 | 17.8 | 93.6 | 2.31 | 23.37 | 0.53 |
| N/P 0.67 | 695.12 | 1.76 | 771.96 | 17.95 | 90.0 | 2.11 | 23.16 | 0.54 |
| N/P 1.33 | 505.75 | 3.72 | 527.79 | 19.23 | 95.8 | 3.56 | 15.83 | 0.58 |
| N/P 4.0 | 467.52 | 2.63 | 506.85 | 17.8 | 92.2 | 3.28 | 15.21 | 0.53 |

Conclusion
Addition of PEI to DNA does not inhibit the binding of Picogreen®. Therefore any protection afforded to DNA during the liposome encapsulation method even with PEI included within the formulation must come from lipid encapsulation.

Example 3

The following experiment was conducted to investigate whether cationic lipid can be removed from the liposome composition.
Method
Lipid Formulation=DOTAP/DOPC/Chol/PEG-DSG/
DiI(3)-DS 30/1500/1000/30/3 nmol per 1 μg
DNA Formulation 1: Lipid as above mixed with DNA (plus PEI N/P=0.9)
Formulation 2: DNA plus PEI N/P=0.9
Formulation 3: Lipid as above mixed with DNA
Formulation 4: Lipid as above (except no DOTAP) mixed with DNA (plus PEI N/P=0.9)
Results

| Formulation | % Dye Access | Stdev | Size nm |
|---|---|---|---|
| 1 | 21.5 | 0.9 | 183.5 ± 60 |
| 2 | 93.2 | 2.4 | N.D |
| 3 | 31.2 | 1 | 248.8 ± 67.2 |
| 4 | 24.0 | 0.7 | 289.6 ± 112.5 |

Conclusion
Using the DNA pre-contacted with a polyamine or polymeric amine, liposomal particles can be made without using any cationic lipid, that entrap >75% of the DNA.

Example 4

Additional studies were performed to study the effect of single-chain cationic surfactants.
Method
The liposomes were prepared as in Example 3, Formulation 1, except that Hexadecyltrimethylammonium bromide (HTAB) and tetradecyltrimethylammonium bromide (TTAB) were used instead of DOTAP.

| Formulation | % Dye Accessibility | Size nm |
|---|---|---|
| HTAB | 31.6 ± 0.6 | 202.8 ± 48.3 |
| TTAB | 27.6 ± 0.8 | 193.4 ± 69.0 |

Conclusion
Single-chain cationic amphiphiles can be used to make low-cationic-lipid liposomes with polyamine/polymeric amine pre-condensed DNA.

Example 5

To test if the pre-contacting of DNA with polyamine or a polymeric amine enables the DNA to be entrapped efficiently within neutral lipid liposomes that do not contain any cationic lipid. DiI(3)-DS is included for purposes of facilitating the experiments, but would not typically be included in liposomes for therapeutic use.
Method
Formulation 1: DOTAP/DOPC/Chol/PEG-DSG/DiI(3)-DS 0/1500/1000/30/3 nmol per μg DNA
Formulation 2: DOTAP/DOPC/Chol/PEG-DSG/DiI(3)-DS 0/1500/1000/30/3 nmol per μg DNA (plus Spermine N/P=1)
Formulation 3: DOTAP/DOPC/Chol/PEG-DSG/DiI(3)-DS 30/1500/1000/30/3 nmol per μg DNA (plus Spermine N/P=0.9)
Results

| Formulation | % Dye Accessibility | Size nm |
|---|---|---|
| 1 | 80.3 ± 4.3 | 260.7 ± 70.9 |
| 2 | 26.2 ± 0.9 | 193.4 ± 69.0 |
| 3 | 32.2 ± 1.1 | 194.3 ± 47.3 |

Conclusions
In the absence of cationic lipid, the addition of a polyamine or polymeric amine such as the one that acts as a nucleic acid-condensing agent, e.g., spermine, to the nucleic acid solution leads to efficient encapsulation DNA within neutral lipid liposomes using organic-aqueous monophase method. Without a polyamine or a polymeric amine, the DNA is not efficiently entrapped.

Example 6

Using the formulation of DOPC/Chol (3:2) and 1% PEG-DSG with spermine precondensed DNA with N/P=1, the dependence of DNA entrapment and particle size on the total amount of lipid is tested.
Method
Particles made as in Example 1.
Lipid Formulation: DOPC/Chol/PEG-DSG
  Formulation A: Lipid ratios 1200/800/20 per µg DNA
  Formulation B: Lipid ratios 1000/667/17.5 per µg DNA
  Formulation C: Lipid ratios 750/500/12.5 per µg DNA
  Formulation D: Lipid ratios 500/333/8.3 per µg DNA
  Formulation E: Lipid ratios 1500/1000/25 per µg DNA
Results

| Formulation | % Dye Accessibility | Size nm |
|---|---|---|
| A | 19.9 ± 0.7 | 182.6 ± 52.8 |
| B | 22.2 ± 0.8 | 201.2 ± 82.2 |
| C | 25.2 ± 0.9 | 193.4 ± 86.2 |
| D | 34.4 ± 1.2 | 222.4 ± 97.0 |
| E | 21.8 ± 0.7 | 213.2 ± 85.0 |

Conclusions

Formulations A, B, and E had dye accessibility of about 20%. Sample C had somewhat higher dye accessibility. The particle with the highest dye accessibility and largest size was sample D. Therefore, lipid amounts of 500/333/8.3 mmol of the components per mg DNA may be too low, and it is preferable to use ratios greater than this. It is also possible that too high ratios may lead to liposomes that do not contain any DNA, so the minimum amount of lipid that stably entraps DNA would be preferable. Therefore sample B or C is optimal.

Example 7

The previous liposomes that combined pH titratable lipids/cationic and neutral lipids were made in such a way that the pH of the solution when mixed was less than 5.5 in order to maximize the electrostatic interactions with DNA. Subsequently, it was found that low pH has a detrimental effect of the activity of both luciferase and GFP encoding plasmid activities.

This study was to see if liposomes that are made using neutral lipid and pre-combining of the DNA with polyamine or polymeric amine have to be at low pH and also if they can be made by mixing at room temperature. Also, the unsaturated lipid HSPC (hydrogenated soy phosphatidylcholine) was used instead of DOPC, and its effects measured.
Method
Formulation 1: DOPC/Chol/PEG-DSG:DNA (plus Spermine N/P=1) (750/500/12.5) per µg DNA
Mixed in such a manner that the pH of the solution was 5.5. Heated for 60° C. for 2 min. Described in detail in Example 1.
Formulation 2: DOPC/Chol/PEG-DSG:DNA (plus Spermine N/P=1) (750/500/12.5) per µg DNA
Mixed in 5 mM Hepes, pH 7.4, 60° C. for 2 min.
Formulation 3: DOPC/Chol/PEG-DSG:DNA (plus Spermine N/P=1) (750/500/12.5) per µg DNA
Mixed in 5 mM Hepes, pH 7.4, 23° C. for 2 min.
Formulation 4: HSPC/Chol/PEG-DSG:DNA (plus Spermine N/P=1) (750/500/12.5) per µg DNA
Mixed in 5 mM Hepes, pH 7.4, 23° C. for 2 min.
Results

| Formulation | % Dye Accessibility | Size nm |
|---|---|---|
| 1 | 21.3 ± 0.9 | 237.6 ± 105.4 |
| 2 | 18.1 ± 0.8 | 233.5 ± 100.5 |
| 3 | 20.0 ± 0.7 | 463.7 ± 223.3 |
| 4 | 96.9 ± 3.2 | 250.8 ± 113.4 |

Conclusions

It appears that mixing at 60° C. is required in order to make liposomes that combine high DNA protection and small size. Mixing at room temperature caused aggregation. The liposomes that were identically prepared except one mixed at pH 5.5 (#1) and the other mixed at pH 7.4 (#2) seem to be very similar in both dye accessibility and size. Therefore, low pH may not be needed to prepare neutral liposomes that contain DNA pre-combined with a polyamine or a polymeric amine (in this case by pre-combined with spermine).

The use of HSPC in this study did not result in entrapped DNA. However, it is possible that the ratios of DNA to lipid or PC/Chol ratio could be optimized to enhance DNA entrapment.

Example 8

The effect of increasing amounts of PEG-DSG in the formulation was studied in the following experiments.
Method
Lipid and DNA were separately dissolved in 50% ethanol/50% 5 mM Hepes, pH 7.4 and heated for 2 mins prior to mixing. DNA was precondensed with spermine at N/P=0.9. Dialysis was performed as above.

| | |
|---|---|
| Formulation 5: DOPC/Chol/Peg-DSG/DiI(3)-DS 1000/667/0/1.67 | 0% PEG-DSG |
| Formulation 6: DOPC/Chol/Peg-DSG/DiI(3)-DS 1000/667/8.33/1.67 | 0.5% PEG-DSG |
| Formulation 7 DOPC/Chol/Peg-DSG/DiI(3)-DS 1000/667/16.7/1.67 | 1.0% PEG-DSG |
| Formulation 8: DOPC/Chol/Peg-DSG/DiI(3)-DS 1000/667/33.3/1.67 | 2.0% PEG-DSG |
| Formulation 9: DOPC/Chol/Peg-DSG/DiI(3)-DS 1000/667/83.3/1.67 | 5.0% PEG-DSG |

Samples were prepared as above and targeted (T) by addition of 15 µg/umol PC of F5-PEG-DSPE antibody-lipid conjugate by an insertion methodology described, e.g., in U.S. Pat. No. 6,210,707. Non-targeted (NT) liposomes are those particles to which no antibody conjugate has been added.
Results

| Formulation | % Dye Accessibility | Size nm |
|---|---|---|
| 5 | 37.0 ± 1.2 | 450.5 ± 209.2 |
| 6 | 42.0 ± 1.4 | 289.2 ± 124.5 |
| 7 | 25.5 ± 0.8 | 216.4 ± 85.4 |
| 8 | 29.3 ± 0.7 | 203.6 ± 89.9 |
| 9 | 23.6 ± 0.8 | 201.6 ± 84.1 |

SKBR3 cells (grown in McCoy's 5A media with 10% FBS) were plated at a density of 100,000 cells/well in a 24 well plate the day previously. DNA was mixed with Lipofectamine™ 2000 as described by the manufacturer's instructions, and 1 µg DNA per well was added to the cells. 1 µg of liposome-encapsulated DNA, and free DNA was also added to each well (in duplicate). After 24 h, the cells were washed and 1 mL media added. After a further 24 h, the cells were assayed for the green fluorescent protein (GFP). This entailed being washed twice with Hank's BSS solution and viewed under a fluorescence microscope for GFP positive cells. GFP expression is calculated as the number of fluorescent cells/total number of cells×100 over many fields of view (n>3).

PEG-DSG content dependence on GFP expression

| Sample# | % PEG-DSG | # cells | # GFP | % GFP | ave | stdev |
|---|---|---|---|---|---|---|
| plated 100,000 cells per well-48 h point | | | | | | |
| 6NT | 0.5 | 67 | 0 | 0 | 0 | 0 |
| 6T | | 81 | 2 | 2.5 | 2.5 | 0 |
| 7NT | 1 | 57 | 0 | 0.0 | 0 | 0 |
| 7T | | 57 | 7 | 12.3 | 9.8 | 3.2 |
| | | 46 | 5 | 10.9 | | |
| | | 64 | 4 | 6.3 | | |
| 8NT | 2 | 71 | 0 | 0.0 | 0.0 | 0.0 |
| 8T | | 81 | 4 | 4.9 | 9.3 | 6.2 |
| | | 76 | 5 | 6.6 | | |
| | | 55 | 9 | 16.4 | | |
| 9NT | 5 | 41 | 0 | 0.0 | 0 | 0 |
| 9T | | 53 | 9 | 17.0 | 15.1 | 6.1 |
| | | 73 | 6 | 8.2 | | |
| | | 45 | 9 | 20.0 | | |
| Lip2000 | | 53 | 13 | 24.5 | 33.2 | 9.4 |
| | | 69 | 22 | 31.9 | | |
| | | 44 | 19 | 43.2 | | |
| DNA | | 52 | 0 | 0.0 | 0 | 0 |
| cells | | 73 | 0 | 0.0 | 0 | 0 |
| plated 30,000 cells per well-48 h point | | | | | | |
| 7NT | 1 | 34 | 0 | 0 | 0 | 0 |
| 7T | | 40 | 3 | 7.5 | 11.5 | 6.0 |
| | | 38 | 7 | 18.4 | | |
| | | 23 | 2 | 8.7 | | |
| 8NT | 2 | 17 | 0 | 0 | 0 | 0 |
| 8T | | 26 | 5 | 19.2 | 16.1 | 9.7 |
| | | 39 | 2 | 5.1 | | |
| | | 21 | 5 | 23.8 | | |
| 9NT | 5 | 43 | 0 | 0.0 | 0 | 0 |
| 9T | | 22 | 5 | 22.7 | 14.1 | 8.4 |
| | | 44 | 6 | 13.6 | | |
| | | 50 | 3 | 6.0 | | |

Conclusions

A certain amount of PEG-DSG is beneficial for optimal liposome formation. Greater than 0.5 mol. % allows for reasonably efficient DNA encapsulation and gives rise to small particles. Less than 0.5 mol. % causes larger particles to form. Increased PEGylation does not inhibit GFP expression.

Example 9

Using the formulation from Example 8, the inclusion of DOPE was studied.
Method
Formulation 9: as above (see Example 8)
Formulation 11: DOPC/DOPE/CholPEG-DSG/DiI(3)-DS (900/100/667/83.3/1.67) per µg DNA (plus spermine N/P=0.9) 10 mol. % DOPE
Formulation 12: DOPC/DOPE/Chol/PEG-DSG/DiI(3)-DS (800/200/667/83.3/1.67) per µg DNA (plus spermine N/P=0.9) 20 mol. % DOPE
Formulation 13: DOPC/DOPE/Chol/PEG-DSG/DiI(3)-DS (600/400/667/83.3/1.67) per µg DNA (plus spermine N/P=0.9) 40 mol. % DOPE Samples were prepared as above and targeted by addition of 15 mg/mmol PC of F5-PEG-DSPE antibody-lipid conjugate. The insertion procedure is initiated by heating at 60° C. for 30 min. The resulting solutions were rapidly cooled in iced water, samples sterilized by passing through 0.45 µm PES filter. Samples were also tested for gene expression by addition to SKBR3 cells, and counting GFP-positive cells 48 h later.
Results

| Sample | DOPE mol % | % Dye Accessibility | Size nm, mean | Stdev (Gaussian) |
|---|---|---|---|---|
| 9NT | 0 | 23.6 ± 0.7 | 201.6 | 84.1 |
| 9T | 0 | 25.6 ± 0.9 | | |
| 11 NT | 10 | 26. ± 0.8 | 206.2 | 72.9 |
| 11 T | 10 | 34.1 ± 1.3 | | |
| 12 NT | 20 | 26.9 ± 1.1 | 223.1 | 101.3 |
| 12 T | 20 | 38. ± 0.6 | | |
| 13 NT | 40 | 33.7 ± 1.4 | 213.1 | 92.7 |
| 13 T | 40 | 39. ± 0.77 | | |

Transfection Efficiency

| # | DOPE mol % | # cells | # GFP+ | % GFP | ave | stdev |
|---|---|---|---|---|---|---|
| 9NT | 0 | 44 | 0 | 0 | 0 | 0 |
| 9T | 0 | 38 | 7 | 18.4 | 23.1 | 6.3 |
| | | 34 | 7 | 20.6 | | |
| | | 33 | 10 | 30.3 | | |
| 11 NT | 10 | 36 | 0 | 0 | 0 | 0 |
| 11 T | 10 | 49 | 8 | 16.3 | 16.7 | 3.6 |
| | | 39 | 8 | 20.5 | | |
| | | 30 | 4 | 13.3 | | |
| 12 NT | 20 | 40 | 0 | 0 | 0 | 0 |
| 12 T | 20 | 32 | 9 | 28.1 | 23.4 | 6.6 |
| | | 32 | 6 | 18.8 | | |
| 13 NT | 40 | 47 | 0 | 0 | 0 | 0 |
| 13 T | 40 | 40 | 2 | 5.0 | 10.5 | 6.9 |
| | | 36 | 3 | 8.3 | | |
| | | 33 | 6 | 18.2 | | |
| Lipo2000 | | 26 | 13 | 50.0 | 60.0 | 14.1 |
| | | 10 | 7 | 70.0 | | |
| DNA + Spermine 1:0.9 | | 35 | 0 | 0.0 | 0.0 | 0.0 |
| | | 46 | 0 | 0.0 | | |
| DNA | | 49 | 0 | 0 | 0.0 | 0.0 |
| cells | | 42 | 0 | 0 | 0 | 0 |

Conclusions

Contrary to the conventional view on the role of DOPE as a "helper" lipid for transfection by lipid-based carriers, inclusion of DOPE did not increase the transfection efficiency of these liposomes. On the contrary, it is notable that targeted samples containing DOPE have substantially higher dye accessibilities than corresponding samples having less than 10% DOPE. In addition, spermine on its own does not cause DNA to be expressed intracellularly, indicating that it is the combination of the targeted-liposome entrapping precondensed DNA that causes gene expression.

Example 10

To measure the effect of pH on the activity of reporter plasmids after incubation in 50% ethanol aqueous solutions at 60° C., the following experiment was performed.

Methods

GFP and luciferase reporter plasmids were prepared in buffered solutions of pH ranging from approximately 4 to 7.2 at 50 µg/ml DNA concentration from stock DNA solutions in TE, pH 8.0 buffer. To span the appropriate pH range, the two chosen buffers were Hepes and MES, both at a concentration of 5 mM. To a 1 mL aliquot of the above solutions, equal volumes of ethanol were added, mixed, and the resultant solutions incubated at 60° C. for 10 min. After cooling, the samples were dialysed against Hepes buffered saline, (HBS), pH 7.25 overnight. The samples were sterile filtered under aseptic conditions and the DNA concentrations were determined by UV absorbance at 260 nm.

SKBR3 cells (grown in McCoy's 5A media with 10% FBS) were plated at a density of 100,000 cells/well in a 24 well plate the day previously. DNA was mixed with Lipofectamine™ 2000 as described by the manufacturer's instructions, and 1 µg DNA per well was added to the cells. After 6 h, the cells were washed and 1 mL media added. After a further 18 h, the cells were assayed for the respective reporter gene. For GFP plasmid this entailed being washed twice with Hank's BSS solution and viewed under a fluorescence microscope for GFP-positive cells, or for luciferase expression by lysing in a 0.1M sodium phosphate solution and reading luciferase using a luminometer after injection with luciferin. A standard curve was prepared by using purified luciferase, and protein measured by using the MicroBCA™ assay (Pierce). GFP expression is calculated as the number of fluorescent cells/total number of cells×100 over many fields of view (n>3). Luciferase quantity was expressed as ng luciferase per µg total protein. Results are shown below. Both graphs were normalized to the expression obtained from Lipofectamine™ 2000 complexes with DNA from the respective stock solutions i.e., DNA had not been processed by adding ethanol and heating. "Effect of pH of cells expressing GFP" means the effect of GFP-encoding plasmid DNA preincubation in 50% ethanol at various pH on the DNA cell-transfection activity.

Conclusions

Figure 1B:
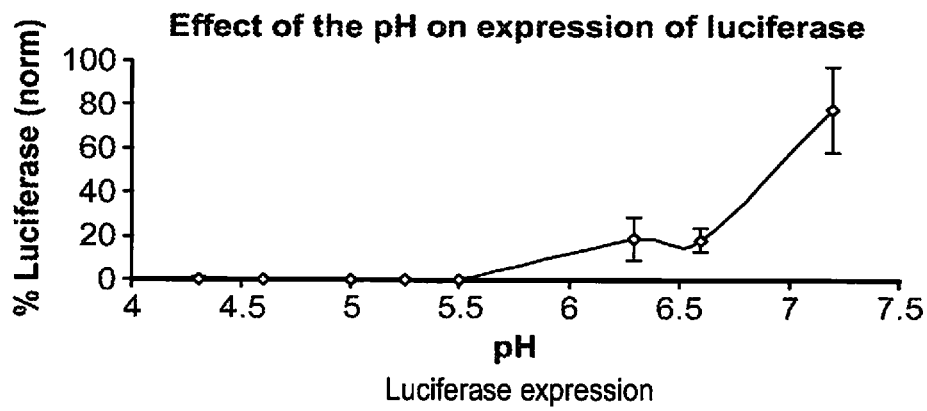

Heating plasmid DNA at pH below 7 in aqueous ethanol solutions at 60° C. for 10 minutes inactivates the plasmid to various degrees (FIG. 1). This process is not specific to the sequence of GFP gene, because it is also observed with luciferase reporter gene.

Example 11

To test the effect of minimum DNA exposure time in 50% ethanol at low pH on the transfection activity of the DNA, the following experiment was performed.

Method

In order to minimize the exposure of DNA to low pH environments, it was decided to optimize the mixing conditions in 50% ethanol, so that the DNA would be heated in a buffer of higher pH, and only when combined with the lipid containing ethanolic solution would the pH be decreased to levels suitable for interaction with pH-titratable lipids (pH 5.5).

Figure 2:
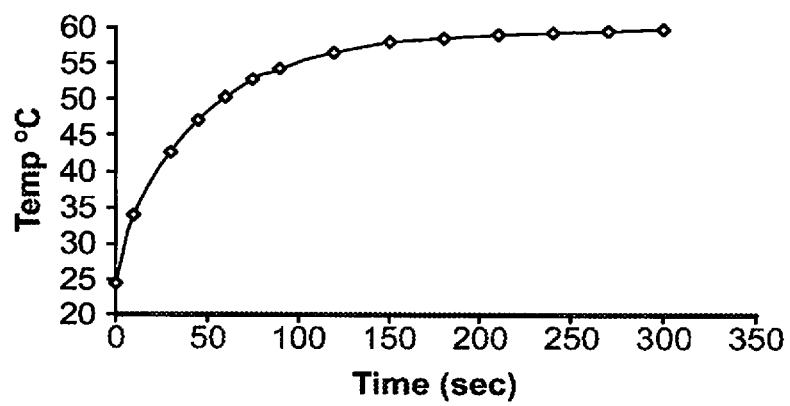
FIG. 2 is a graph showing the time course of temperature equilibration of 50 vol. % ethanol solution, after immersion in 60° C. oil bath.

Firstly, the amount of time needed for solutions to reach 55-60° C. was determined. Results are shown in FIG. 2. It was found that about two minutes is sufficient for solution to reach desired temperature.

Secondly, to minimize the exposure of DNA to low pH conditions, it was recommended to prepare and pre-heat the DNA solution at pH above 7.0 and relatively low buffer (for example, TE, 5 mM Tris-HCl, 2 mM EDTA pH 8.0), and then mix with pre-heated lipid solution of lower pH and/or stronger buffer, and then cool down quickly. It was found that a solution of 2 mM TE buffer (2 mM Tris, 0.4 mM EDTA) pH 8.0 when combined with an equal volume of 20 mM MES, pH 5.1 yields a solution of pH 5.5.

DNA (50 µg) in an ethanolic solution (50% v/v) of 2 mM TE buffer was mixed with an equal volume of an ethanolic solution (50% v/v) of 20 mM MES, pH 5.1 after incubation at 60° C. for 2 min, and the resultant solution dialysed, sterilized by microfiltration, and its transfection activity was studied using Lipofectamine™ 2000 as described above. The results were as follows: untreated DNA (positive control) 100±1.4%; treated DNA, 72.7±9.7%.

Conclusion

Treating DNA in the above manner minimizes the damage done to the plasmid, and retains greater than 70% of the reporter gene activity.

Example 12

A set of liposomes were made so that the net electrical charge on the liposomes was varied from negative to positive, accomplished by altering the ratio of cationic lipid to DNA in the formulation. Liposomes were prepared using a cationic lipid, neutral zwitterionic phospholipids DOPC and DOPE, cholesterol, a PEGylated lipid and a fluorescent lipid (to aid visualization of particles) in such a manner that only the amount of cationic lipid was varied, using the formulation DOSPA/DOPC/Chol/DOPE/PEG-DSG/DiI(3)-DS where the composition was X/15/10/4/0.3/0.03 nmol/µg DNA.

A proportion of each samples was rendered HER2 targeted by insertion of F5-PEG(2000)-DSPE conjugate at a ratio of 15 ug/umol phospholipid, described previously (M. E. Hayes et al., Genospheres: self-assembling nucleic acid-lipid nanoparticles suitable for targeted gene delivery, *Gene Ther.* 13 (2006) 646-651).

After the liposomes were made, they were tested for DNA entrapment and ability to interact with cultured human cancer cells that over-express the HER2 receptor (SKBR3), by fluorescence microscopy (FIG. 3).

Measuring DNA Entrapment Efficiency

Typically, DNA (or siRNA/oligonucleotide) entrapment is measured by a simple, quick fluorescence based assay called the Picogreen® Dye Accessibility Assay. It is based around an idea that a molecule such as Picogreen® (Invitrogen) is highly fluorescent once bound to DNA. In its unbound state it has low fluorescence. Once Picogreen® is added to a solution of liposomes it quickly binds to any "accessible" DNA, thus exhibiting fluorescence. This accessible dye may be bound to totally unencapsulated DNA (free DNA) or DNA that is partially or poorly encapsulated. The dye does not cross lipid bilayers; therefore any DNA that is properly encapsulated will be shielded from the dye. If the liposomes are disrupted and the DNA is released (by means of adding a detergent solution), then Picogreen® has the ability to bind the total amount of DNA present. By extrapolation to standard curves, the concentration of accessible and total DNA can be measured. The ratio of each gives us the "% Dye Accessibility" and is calculated as follows:

% Dye Accessibility=[DNA]$_{absence\ of\ detergent}$/[DNA]$_{presence\ of\ detergent}$×100

Figure 4:
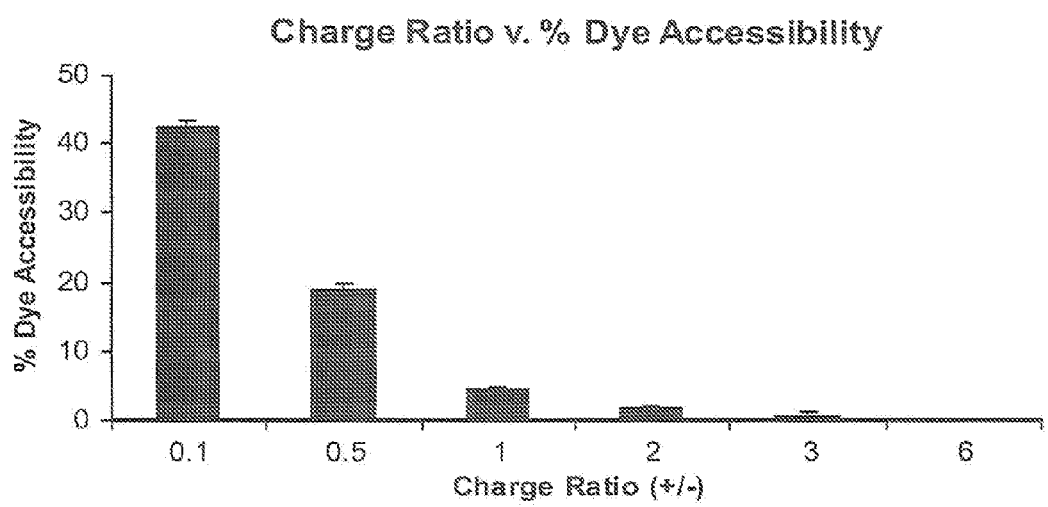
FIG. 4 is a graph showing the % dye accessibility of liposomes prepared by varying the amount of the cationic lipid component, keeping other components constant. The formulation was DOSPA/DOPC/Chol/DOPE/PEG-DSG/DiI(3)-DS where the composition was X/15/10/4/0.3/0.03 nmol/µg DNA.
Figure 5:
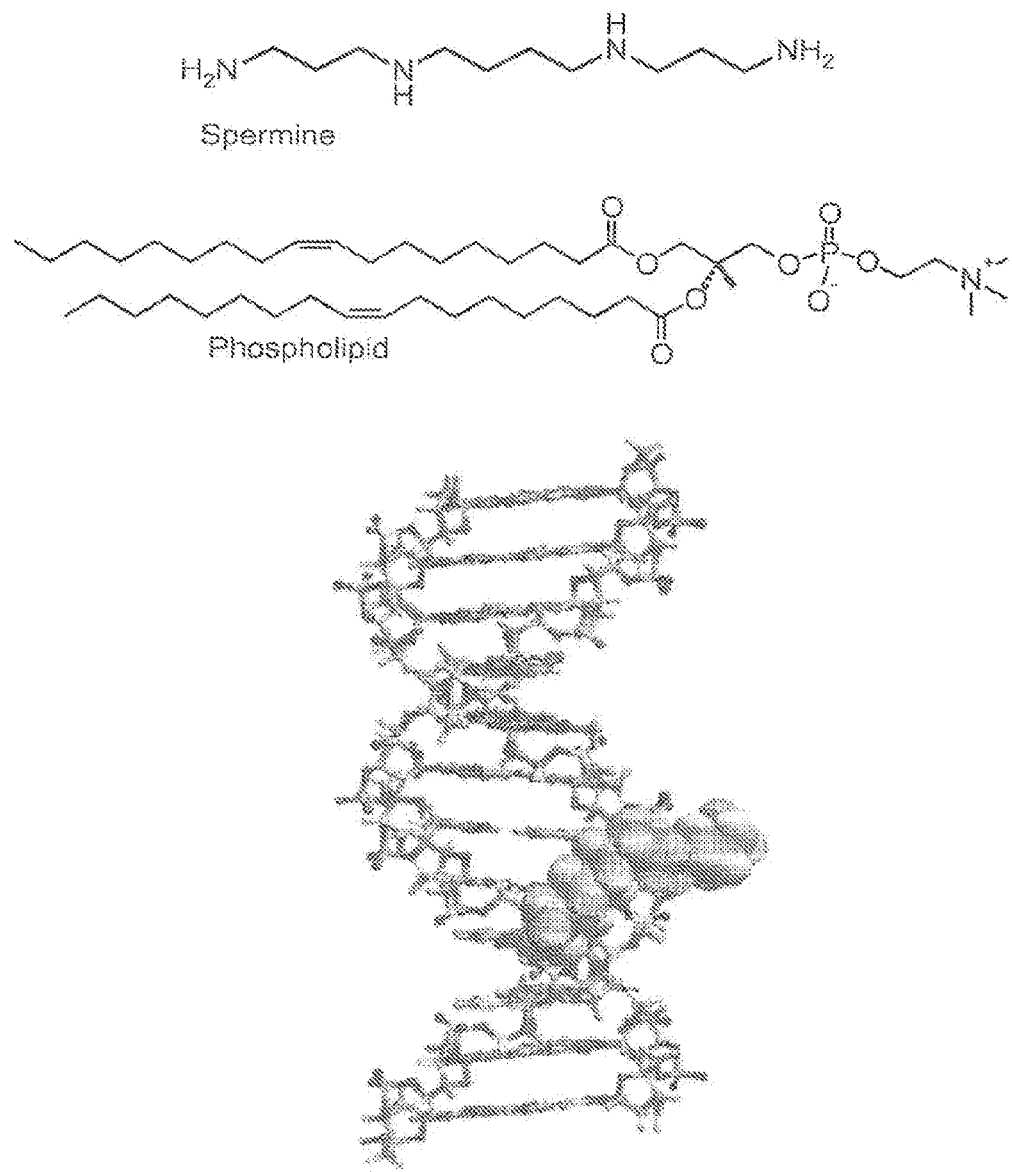
FIG. 5 shows the chemical structures of spermine, a typical phospholipid, dioleoyl-sn-glycero-phosphatidylcholine (DOPC) and a 3D depiction of spermine interaction with DNA double helix.

In delivering targeted nucleic acid liposomes, there exist many major hurdles, including the need to efficiently entrap DNA within the liposome, without having a highly cationic charge, in fact having an overall charge less than 1/1 as this is preferable to prevent non-specific cell interactions. However, at cationic ratios less than +/−<1, the efficiency of DNA entrapment decreases dramatically (FIG. 4). It is known that polyamines such as spermine can bind DNA through electrostatic interactions (see, e.g., FIG. 5) and it has been suggested that they can induce conformational changes in the DNA structure (Fuerstein B G et al., Spermine-DNA interactions: A theoretical study, *Proc. Nat. Acad. Sci. USA* August 1986, Vol. 83, pp. 5948-5952). It has been observed that addition of spermine to nucleic acids can confer entrapment into liposomes without the use of any cationic lipid. It has also been found that lower molecular weight nucleic acids, such as 18-mer oligonucleotides and siRNA, can also be effectively entrapped without the use of any cationic lipid.

Description of Study

The following experiments were performed to find the minimum amount of cationic lipid (in this case DOSPA) that could be used in conjunction with spermine to provide optimal oligo encapsulation, while maintain a small size of the liposomes (<200 nm). Liposomes were prepared according to the formulation DOSPA/DOPC/Chol/DOPE/Peg-DSG/DiI(3)-DS varying the amount of DOSPA and spermine while keeping all other lipids constant. The entrapment efficiency, size, filterability (efficiency of passing through a sterilizing 0.2 μm filter) and cellular uptake of liposomes were measured.

Calculating the Cationic Lipid/DNA Phosphate Ratio

DNA Base Pair Molecular Weight=330 g/mol,
=>1 g/330 g mol$^{-1}$=0.00303 mol phosphate per 1 g DNA (or RNA)
i.e., 3.03 nmol phosphate (or phosphorothioate)=11 μg DNA (or RNA)

0.075 nmol DOSPA×4 (headgroup) positive charges per DOSPA=0.3 nmol "positive" charges. Therefore 0.075 nmol DOSPA should neutralize (or combine) with 10% of the total phosphate charges of oligo in 1 ug. Therefore a formulation that corresponds to DOSPA/DOPC/Chol/DOPE/Peg-DSG/DiI(3)-DS in the molar ratios 0.075/30/20/8/1.74/0.058 nmol lipid per 1 μg oligo means that 10% of the total anionic charges emanating from the oligo is complexed. This sample is referred to as DOSPA 0.1. Accordingly, a formulation that has enough DOSPA to bind to 25% of the charges i.e., DOSPA/DOPC/Chol/DOPE/Peg-DSG/DiI(3)-DS with a molar lipid ratio of 0.1875/30/20/8/1.74/0.058 nmol per 1 μg oligo is referred to as DOSPA 0.25. This small amount of cationic lipid was supplemented with spermine to aid entrapment of the oligo, and is indicated below as N/P (referred to as total N from spermine to DNA phosphate).

These formulations were then targeted as described previously (see, e.g., G. Thurston et al., Cationic liposomes target angiogenic endothelial cells in tumors and chronic inflammation in mice, *J. Clin. Invest.* 101 (1998) 1401-1413) and tested for ability to internalize in Her2 overexpressing cells (MCF7 (ATCC® #HTB-22™)/clone18).

Results

Figure 9:
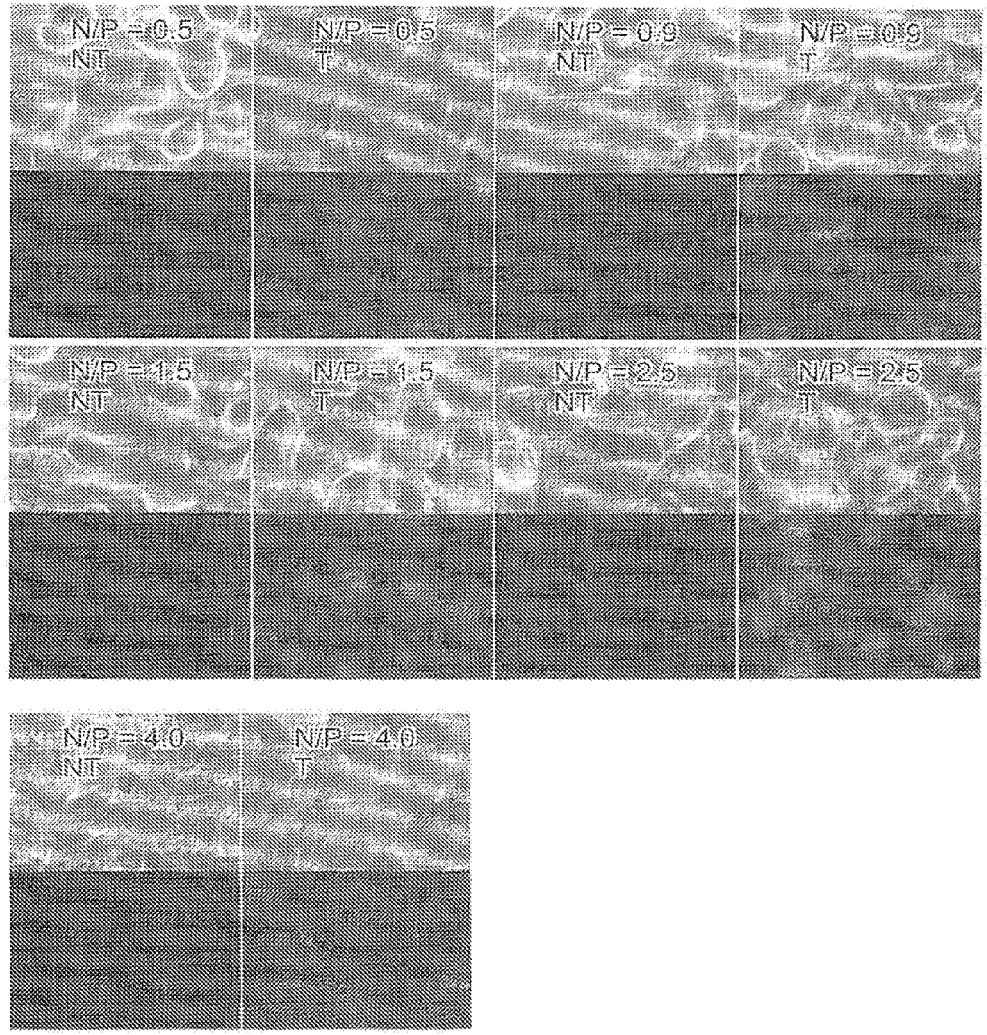
FIG. 9 shows microscopy of MCF7/clone18 cells after 24 h exposure to DiI(3)-DS labeled liposomes-DOSPA (0.1) Formulation (¼ sec fluorescence; 8 sec phase contrast). NT designates plain, "non-targeted" formulations, T "targeted" antiHer2 receptor formulations. N/P indicates the nitrogen/phosphate ratio of DOSPA/DNA respectively.
Figure 10:
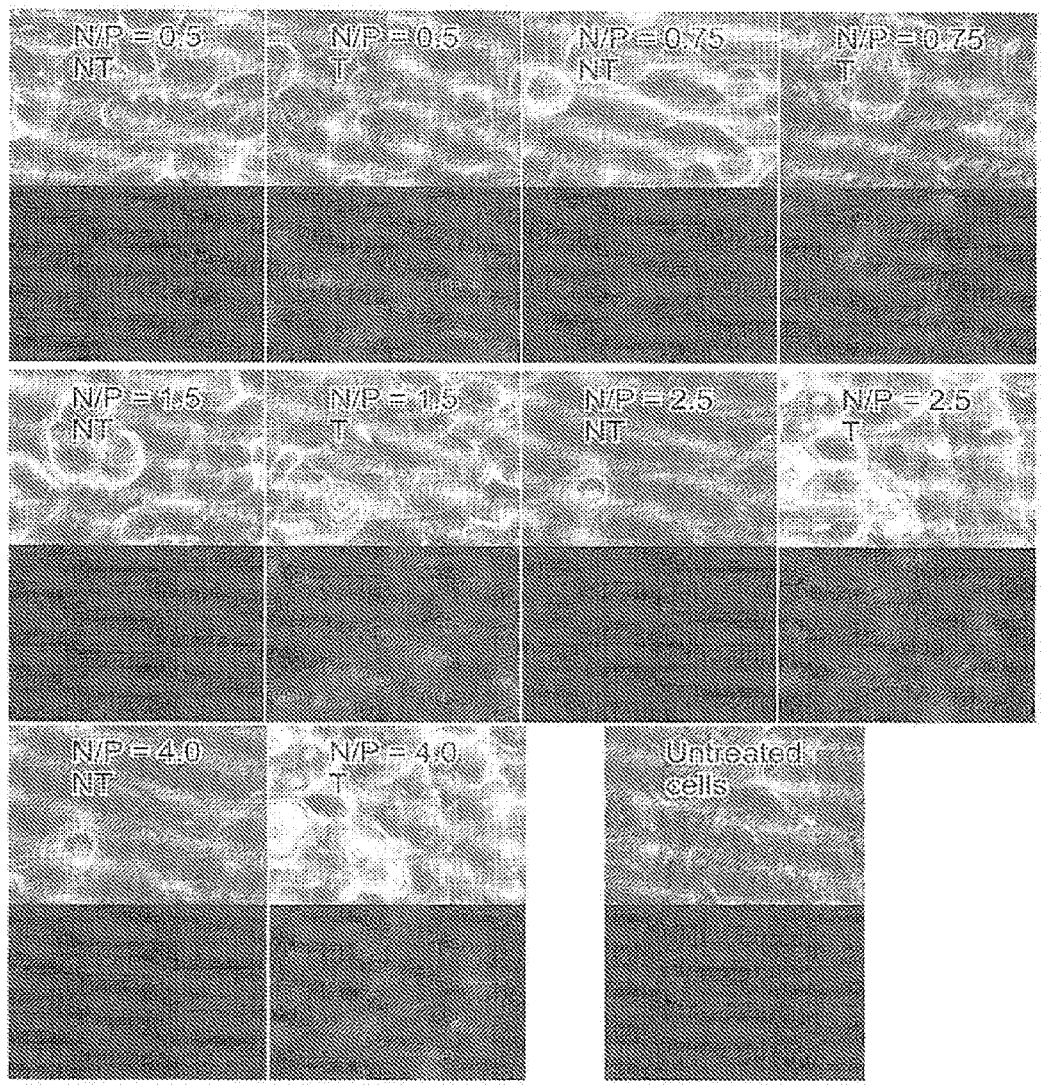
FIG. 10 shows microscopy of MCF7/clone18 cells after 24 h exposure to DiI(3)-DS labeled liposomes-DOSPA (0.25) Formulation (¼ sec fluorescence; 8 sec phase contrast). NT designates plain, "non-targeted" formulations, T "targeted" antiHer2 receptor formulations. N/P indicates the nitrogen/phosphate ratio of DOSPA/DNA respectively.
Figure 11:
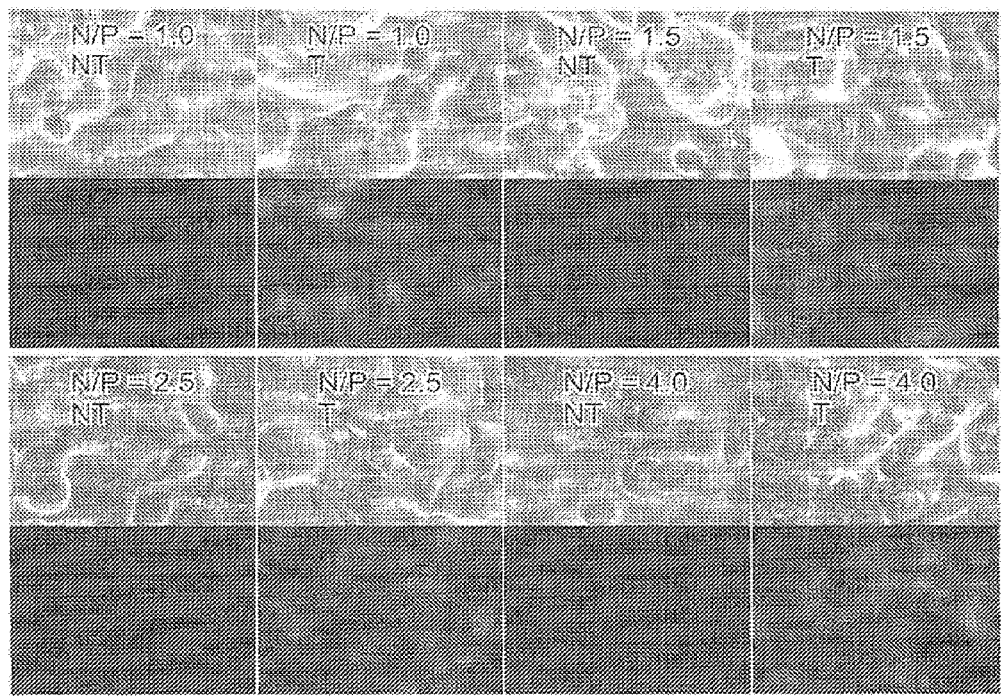
FIG. 11 shows microscopy of MCF7/clone18 cells after 24 h exposure to DiI(3)-DS labeled liposomes-DOSPA (0.25) Formulation (¼ sec fluorescence; 8 sec phase contrast). NT designates plain, "non-targeted" formulations, T "targeted" antiHer2 receptor formulations. N/P indicates the nitrogen/phosphate ratio of DOSPA/DNA respectively.
Figure 12:
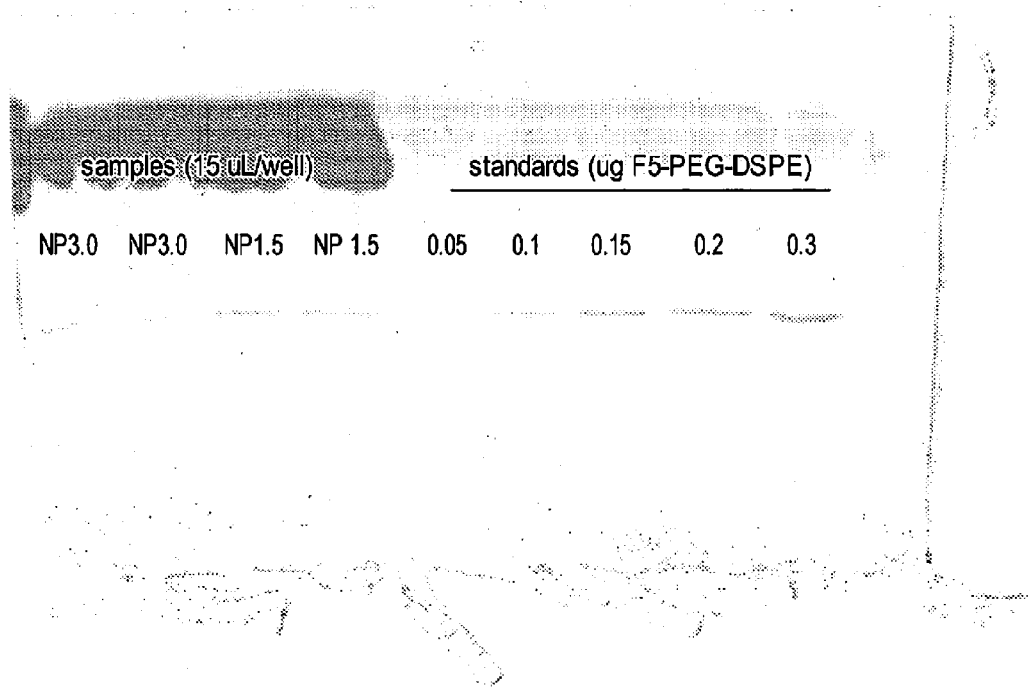
FIG. 12 shows an SDS-PAGE gel showing purified liposomes samples and standards containing varying amounts of F5-PEG-DSPE. The density of the gel bands was determined using Image J software. From extrapolation to the standard curve, the amount of incorporated protein per umol of lipid was 13.64±0.64 and 10.59±0.39 µg/µmol for the N/P=1.5 and N/P=3.0 respectively (in duplicate).

It was found that regardless of the amount of cationic lipid present in the formulation (at sub molar ratios of cationic/anionic charge), spermine at ratios greater than about N/P=0.9 (N/P is the added spermine/oligo phosphate ratio) caused the oligo to become entrapped at high efficiencies (FIGS. 6-8). In the case of the formulation designated "DOSPA 0.1" about 10% of the oligo remained free at an N/P ratio of 0.9. For the formulation designated "DOSPA 0.25" the amount of free oligo was about 5% at an N/P of 0.8 and in the "DOSPA 0.5" formulation, the free oligo was about 5% at the lowest measured value of N/P=1. The size of the particles were approximately the same for all sets of studies and the filterability was greater than 79% in all cases, highest for "0.1" and "0.5" formulations. FIGS. 9-11 show that the liposomes prepared with low amounts of cationic lipid, supplemented with spermine, exhibit highly specific targeted uptake, with no observable non-specific cellular interactions.

Example 13

Description of Study

A 21-23 nt siRNA against the SSB housekeeping gene was tested for encapsulation into liposomes of low cationic lipid content. From previous formulation studies with oligonucleotides it was determined that the formulation having enough DOSPA to bind 10% of the anionic charge from DNA (or RNA) should be used in subsequent studies. The formulation with the lowest amount was selected because it gave similar results as those containing higher levels of DOSPA in terms of encapsulation efficiency and size, but the minimum cationic levels may impart enhanced selectivity for targeting in vivo because of less non-specific interactions with components of the blood stream and endothelium. From FIGS. 6-8, having an excess of spermine, i.e., ratios higher than the minimum for good entrapment, does not seem to impart any negative effects in terms of size, encapsulation efficiency or target specific cellular interaction. Therefore, we chose to pick one individual lipid formulation, using ratios of spermine at N/P=1.5 and 3.0 to test liposome encapsulation and stability during storage.

Lipid Formulation

TABLE 1

Liposome formulation used for testing DNA entrapment (nmol lipid per 100 μg of siRNA)

| DOSPA | DOPC | Chol | PEG-DSG | DiI(3)-DS |
|---|---|---|---|---|
| 7.5 | 1000 | 667 | 50 | 5 |

TABLE 2

Picogreen analysis of liposomes, size measurements and the ratio of phospholipid to siRNA in samples made at N/P = 1.5 and N/P = 3.0

| Sample | % Dye Accessibility ± stdev | Size (nm) ± stdev | Lipid/DNA (Theoretical) (nmol/μg) | Lipid/DNA (Measured) (nmol/μg) |
|---|---|---|---|---|
| N/P = 1.5 Non-targeted | 24.88 ± 0.61 | 159.8 ± 34.8 | 10 | 9.27 ± 0.13 |
| N/P = 1.5 Non-targeted | 19.06 ± 0.38 | 131.9 ± 29.4 | 10 | 8.95 ± 0.23 |

These samples were then rendered ant-Her2 receptor specific by the addition of F5-PEG-DSPE as described earlier, purified on a Sepharose® 4B-Cl column into water, then from concentrated solutions a final storage buffer of 5 mM Hepes, 144 mM NaCl, pH 7.25 (HBS) or 5 mM Hepes, pH 7.25, 10% sucrose (w/w) was made.

The samples were stored overnight either in solution at 4° C. or frozen at −80° C. as described. (Note; after purification on a Sepharose® 4B-Cl column, free (non-encapsulated siRNA) is separated, therefore it is normal that the dye accessibility is lower on purified samples). After purification, the above samples had a % dye accessibilities of (N/P=1.5, NT, F5) and (N/P=3.0, NT, F5) of 15.41±0.61, 18.85±0.32, 14.67±0.58 and 19.37±0.55 respectively.

TABLE 3

Analysis of samples that were stored either at 4° C. or at −80° C. overnight.

| Sample | Storage Buffer | Storage Temperature | % Dye Accessibility | Size (nm) ± stdev |
|---|---|---|---|---|
| NT, N/P = 1.5 | HBS | 4° C. | 13.89 ± 0.26 | 164.5 ± 66.6 |
| | Sucrose | −80° C. | 13.83 ± 0.79 | 162.7 ± 64.8 |
| F5, N/P = 1.5 | HBS | 4° C. | 19.22 ± 1.31 | 158.7 ± 64.8 |
| | Sucrose | −80° C. | 17.25 ± 0.53 | 154.2 ± 68.4 |
| NT, N/P = 3.0 | HBS | 4° C. | 14.15 ± 0.43 | 151.0 ± 63.9 |
| | Sucrose | −80° C. | 12.98 ± 0.32 | 150.9 ± 52.5 |

TABLE 3-continued

Analysis of samples that were stored either at 4° C. or at −80° C. overnight.

| Sample | Storage Buffer | Storage Temperature | % Dye Accessibility | Size (nm) ± stdev |
|---|---|---|---|---|
| F5, N/P = 3.0 | HBS | 4° C. | 18.15 ± 0.35 | 149.0 ± 64.1 |
|  | Sucrose | −80° C. | 16.56 ± 0.39 | 145.4 ± 64.2 |

Results

Liposomes can be targeted by co-incubation with F5-PEG-DSPE micelles and heating at 37° C. overnight. The initial amount of protein conjugate that was added was 15 μg/umol PL. Upon purification of liposomes from non-incorporated conjugate, the amounts of conjugate associated with the liposomes was 13.64±0.64 and 10.59±0.39 for the two formulations tested. This represents a great than 70% incorporation efficiency. This indicates that liposomes that contain siRNA and low amounts of cationic lipids can readily be targeted by this method.

Nucleic acids in general, but more specifically siRNA/shRNA are extremely sensitive to degradation during storage, and are best stored frozen. Special handling precautions are recommended for working with siRNA/shRNA. RNases are abundant are present on most surfaces that come into human contact and should be thoroughly cleaned with special RNase removing solutions. In short, it is very easy to cause siRNA/shRNA degradation through even the most careful handling procedures. As the knockdown effect of RNAi is so sequence-specific, partial degradation often adversely effects the ability of a given siRNA/shRNA to have the desired knockdown effect. Therefore, storing the liposomes in a medium that prevents either chemical degradation and/or biological degradation from nucleases would be of great benefit.

The hypothesis that liposomes could be stored frozen by combining with a cryoprotectant solution of 10% sucrose before freezing was tested. Sucrose is known to aid in the freezing of liposomes by keeping the phospholipid headgroup hydrated and preventing lipid realignment and bilayer deformation.

From the above results it was observed that freezing liposomes in the presence of sucrose has no adverse effect on the size or siRNA entrapment efficiency compared to those samples kept refrigerated in buffered saline. Assuming that 24 h is representative of longer times in a frozen state, this may give liposomes a longer shelf life and protect them from either lipid or nucleic acid degradation.

Special Precautions in Preparing Liposomes with siRNA/shRNA

The present process allows for assembly of DNA-lipid liposomes in an environment where particle-forming lipids would not form a condensed phase beyond a micelle, and the DNA would still be soluble by itself prior to combination. It was found that such conditions could be satisfied in a number of different organic solvent/water mixtures including 50% (v/v) ethanol. However, this is usually achieved by heating the lipid and DNA solution prior to combination. For encapsulation of closed circular plasmid DNA, the optimal temperature was found to be 60° C. However, it is well known that shorter pieces of DNA (and RNA) can "melt" or denature at lower temperatures. DNA melting is the process by which double-stranded (deoxy)ribonucleic acid unwinds and separates into single-stranded strands through the breaking of hydrogen bonding between the bases.

RNAi is an RNA-dependent gene silencing process that is controlled by the RNA-induced silencing complex (RISC) and is initiated by short double-stranded RNA molecules in a cell's cytoplasm. Therefore the delivery of double-stranded siRNA is very important. Denaturation of siRNA or shRNA before encapsulation would likely result in a non-active particle; therefore it is prudent to measure the melting temperature of each siRNA or shRNA sequence prior to encapsulation.

In order to measure the melting temperature (Tm) (or siRNA melting transition temperature, defined as the temperature at which 50% of the siRNA is in the single-stranded form and 50% in the double-stranded form), siRNA was diluted in the buffer of choice (see Table 4) and the absorbance at 260 nm measured at various temperatures. An increase in absorbance at 260 nm is indicative of siRNA strand unwinding (see FIG. 13).

TABLE 4

A description of the buffers used in the siRNA melting study, the calculated Tm and the sequence of each siRNA.

| siRNA | Buffer | Tm ° C. |
|---|---|---|
| Ssb | 5 mM Hepes, pH 7.25 | 41.5 |
| Ssb | Ethanol/5 mM Hepes, pH 7.25 | 53.0 |
| Ctrl | 5 mM Hepes, pH 7.25 | 57.0 |
| Ctrl | Ethanol/5 mM Hepes, pH 7.2 | 568.0 |

Relatively small changes in the sequence of siRNA or shRNA can dramatically affect the duplex thermostability. In particular, A-U rich base pairing at the ends can make the duplex unstable at the end and lead to unwinding. We tested the SSB and control siRNA in the solutions that typically are used for microparticle/liposome preparation. A low ionic strength buffer such as 5 mM Hepes, pH 7.25 in a 50/50 mixture with ethanol is a preferred buffer. In order to maintain duplex form, preparation of liposomes with SSB siRNA or shRNA should take place at a temperature lower than 53° C. We measured the encapsulation efficiency and size of liposomes containing SSB siRNA at 40° C. and 45° C.

TABLE 5

Analysis of liposomes containing SSB siRNA made at 40° C. and 45° C.

| sirna | temp ° C. | % dye ac | stdev | size (nm) | stdev |
|---|---|---|---|---|---|
| Ssb | 40 | 29.66 | 0.97 | 135.1 | 38.1 |
| Ssb | 45 | 25.29 | 1.04 | 152.1 | 61.7 |
| Control | 45 | 28.97 | 0.67 | 131.5 | 55.1 |

Figure 13:
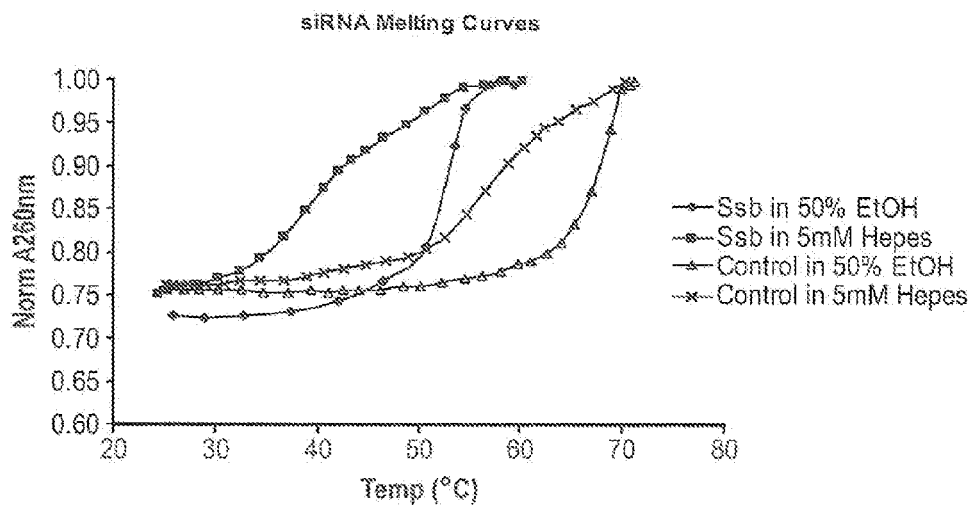
FIG. 13 shows the absorbance at 260 nm of various siRNA solutions at temperatures.

FIG. 13 shows that the control siRNA is stable at 45° C. to unwinding. Therefore, we used this temperature as a stable temperature to compare to liposomes containing the less stable SSB siRNA at 45° C. and at a lower temperature, 40° C. The microparticle/liposome formulation was DOSPA/DOPC/Chol/Peg-DSG/DiI(3)-DS in the ratio 7.5/1000/667/50/5 nmol per 100 μg siRNA with a spermine ratio of N/P=1.5

Preparation of SSB liposomes at the lower temperature had no adverse effects on entrapment efficiency and size using this low cationic lipid containing formulation. Therefore, it is possible to prepare the liposomes at a relatively low temperature in order to minimize melting and still retain good entrapment.

Figure 14:
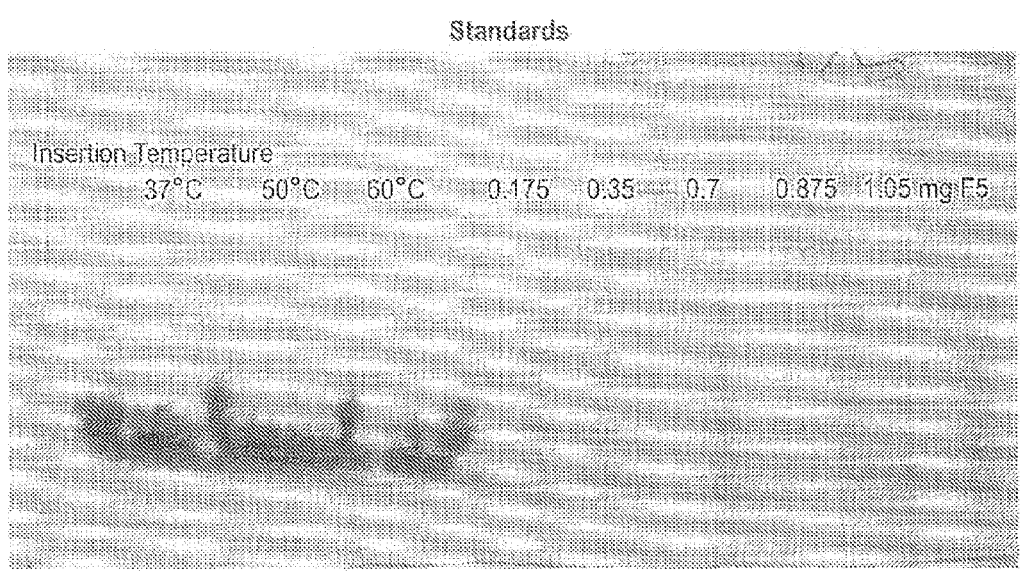
FIG. 14 shows an SDS-PAGE gel showing F5-PEG-DSPE content of purified liposomes that were heated at various temperatures to test insertion efficiency of targeting conjugate.

In addition, the insertion of the targeting ligand for plasmid liposomes usually takes place at 60° C. The insertion efficiency of the same liposomes containing SSB siRNA at lower temperatures was tested in order to evaluate if liposomes can be targeted by this methodology without elevated temperatures (see FIG. 14).

TABLE 6

Measured F5-PEG-DSPE content in purified liposomes, incubated at temperatures indicated for 30 min.

| Sample | Insertion T (° C.) | Int in lane | Calc'd F5 ug | [PO4]mM | PL/well | Measured F5/PL ug/umol | Initial F5/PL ug/umol | % Insertion |
|---|---|---|---|---|---|---|---|---|
| 1 | 37 | 439.042 | 0.464 | 0.32 | 0.0384 | 12.07 | 15 | 80.5 |
| mh53; 12 | 50 | 542.042 | 0.577 | 0.381 | 0.04572 | 12.62 | 15 | 84.1 |
|  | 60 | 410.456 | 0.432 | 0.342 | 0.04104 | 10.53 | 15 | 70.2 |

Results

It was found that incorporation of targeting ligand (F5-PEG-DSPE) could be efficiently performed at lower temperatures, making the degradation of siRNA (or shRNA) less likely. The liposome formulation mostly consists of DOPC and cholesterol, and the low lipid transition temperature likely aids incorporation of the scFv-lipid conjugate into the bilayer.

Conclusions

Short sequences of RNA and short oligonucleotides can be entrapped in liposomes that contain either no cationic lipid, or very small amounts of cationic lipid, and will help the liposome formation process and provide more reproducible formulations. The amount of cationic lipid in a formulation is typically less than 0.5% total lipid, which is far less than used in many alternative formulations, e.g. typical non-targeted SNALP formulations contain 30% cationic lipid, rendering them useful for targeting such organs as liver, but not ideal for reaching distal tumor sites for targeted delivery (Morrissey D V et al., Potent and persistent in vivo anti-HBV activity of chemically modified siRNAs, *Nature Biotechnology* (2005) August; 23(8): 1002-7).

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A composition for introducing a nucleic acid into a cell, the composition comprising:
   a liposome in an aqueous medium, the liposome having an interior and an exterior, wherein the liposome comprises:
   a nucleic acid;
   a polyamine that is spermine, spermidine, or putrescine; and
   a lipid component;
   wherein the lipid component comprises a neutral lipid and cationic lipid wherein less than 0.5 mol % of the total lipid component is cationic lipid, and
   wherein the nucleic acid and the lipid component are present at a ratio of from 5 to 20 nmol lipid per microgram of the nucleic acid, and wherein the liposome is from 30 to 500 nanometers in diameter.

2. The composition of claim 1 wherein, the interior comprises an enclosed interior volume containing the nucleic acid.

3. The composition of claim 2, further comprising an internalizing antibody or a fragment thereof attached to the exterior of the liposome, wherein the antibody or fragment binds to a specific cell surface antigen.

4. The composition of claim 1, wherein the total lipid component comprises less than 0.1% by weight cationic lipid.

5. The composition of claim 1, wherein the lipid component is essentially free of cationic lipid.

6. The composition of claim 1, wherein the liposome is from 70 to 300 nanometers in diameter.

* * * * *